US009017812B2

(12) United States Patent
Takezaki et al.

(10) Patent No.: US 9,017,812 B2
(45) Date of Patent: Apr. 28, 2015

(54) PROCESS OF PRODUCING POLYLACTIC ACID-BASED RESIN MICROPARTICLES, POLYLACTIC ACID-BASED RESIN MICROPARTICLES AND COSMETICS

(75) Inventors: Hiroshi Takezaki, Nagoya (JP); Hiroshi Kobayashi, Nagoya (JP); Makiko Saito, Nagoya (JP); Itaru Asano, Nagoya (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/982,804

(22) PCT Filed: Dec. 22, 2011

(86) PCT No.: PCT/JP2011/079776
§ 371 (c)(1),
(2), (4) Date: Jul. 31, 2013

(87) PCT Pub. No.: WO2012/105140
PCT Pub. Date: Aug. 9, 2012

(65) Prior Publication Data
US 2013/0309497 A1 Nov. 21, 2013

(30) Foreign Application Priority Data

Jan. 31, 2011 (JP) .................................. 2011-018041
Jun. 30, 2011 (JP) .................................. 2011-145913
Nov. 24, 2011 (JP) .................................. 2011-256061

(51) Int. Cl.
*B32B 5/16* (2006.01)
*A61K 9/14* (2006.01)
(Continued)

(52) U.S. Cl.
CPC ... *A61K 8/85* (2013.01); *C08J 3/14* (2013.01); *C08J 9/26* (2013.01); *C08J 9/28* (2013.01);
(Continued)

(58) Field of Classification Search
USPC ............................. 428/402; 424/502; 562/590
See application file for complete search history.

(56) References Cited

U.S. PATENT DOCUMENTS 8,574,669 B2 * 11/2013 Asano et al. ................... 427/212
8,575,254 B2 * 11/2013 Yamamura et al. ........... 524/417
(Continued)

FOREIGN PATENT DOCUMENTS

EP      2 623 542          8/2013
JP      2000-007789 A      1/2000
(Continued)

OTHER PUBLICATIONS

R. Gref et al., Development and characterization of CyA-loaded poly(lactic acid)-poly(ethylene glycol)PEG micro—and nanoparticles. Comparison with conventional PLA particulate carriers, European J. of Pharmaceutics and Biopharmaceutics 51 (2001) 111-118.*

(Continued)

*Primary Examiner* — Holly Le
(74) *Attorney, Agent, or Firm* — DLA Piper LLP (US)

(57) ABSTRACT

A process of producing polylactic acid-based resin microparticles includes a dissolving process that forms a system, which can cause phase separation into two phases of a solution phase mainly composed of polylactic acid-based resin (A) and a solution phase mainly composed of polymer (B) different from polylactic acid-based resin, by dissolving the polylactic acid-based resin (A) and the polymer (B) different from polylactic acid-based resin in an ether-based organic solvent (C), an emulsion-forming process that forms an emulsion by applying a shear force to the system, and a microparticle-forming process that precipitates polylactic acid-based resin microparticles by contacting the emulsion with a poor solvent which has lower solubility of the polylactic acid-based resin (A) than the ether-based organic solvent (C).

6 Claims, 6 Drawing Sheets

(51) Int. Cl.
*A61K 8/85* (2006.01)
*C08J 3/14* (2006.01)
*C08J 9/26* (2006.01)
*C08J 9/28* (2006.01)
*G03G 9/08* (2006.01)
*G03G 9/087* (2006.01)
*A61Q 1/02* (2006.01)
*A61Q 1/10* (2006.01)
*A61K 8/02* (2006.01)
*C08G 63/08* (2006.01)

(52) U.S. Cl.
CPC ........... *C08J2367/04* (2013.01); *G03G 9/0804* (2013.01); *G03G 9/08722* (2013.01); *G03G 9/08762* (2013.01); *G03G 9/08775* (2013.01); *A61Q 1/02* (2013.01); *A61Q 1/10* (2013.01); *A61K 8/0241* (2013.01); *A61K 2800/412* (2013.01); *C08G 63/08* (2013.01); *G03G 9/0802* (2013.01); *G03G 9/0821* (2013.01); *A61K 8/0279* (2013.01)

(56) References Cited

U.S. PATENT DOCUMENTS

2011/0020225 A1* 1/2011 Chung et al. .................. 424/9.1
2013/0337263 A1* 12/2013 Asano et al. .................. 428/402

FOREIGN PATENT DOCUMENTS

| JP | 2001-288273 A | 10/2001 |
| JP | 2004-269865 A | 9/2004 |
| JP | 2005-002302 A | 1/2005 |
| JP | 2005-200663 A | 7/2005 |
| JP | 2009-242728 A | 10/2009 |
| JP | 2012-011268 A | 1/2012 |
| WO | 2009/142231 A1 | 11/2009 |

OTHER PUBLICATIONS

Saravanakumar et al., Polylactic acid microspheres as a potential vaccine delivery system for the tetanus toxoid: Preparation and In Vitro dissolution study, Research J. Pharm. and Tech. 1(4): Oct.-Dec. 2008.*

Yang et al., Development of highly porous large PLGA microparticles for pulmonary drug delivery, Biomaterials 30 (2009) 1947-1953.*

Translation JP 2004-269865 (2004).*

Supplementary European Search Report dated Sep. 24, 2013 from corresponding European Patent Application No. EP 11 85 7597.

* cited by examiner

PRIOR ART

PRIOR ART

PRIOR ART

PROCESS OF PRODUCING POLYLACTIC ACID-BASED RESIN MICROPARTICLES, POLYLACTIC ACID-BASED RESIN MICROPARTICLES AND COSMETICS

TECHNICAL FIELD

This disclosure relates to a process of producing polylactic acid-based resin microparticles, polylactic acid-based resin microparticles and a cosmetic using thereof.

BACKGROUND

Different from polymer molded products such as films, fibers, injection molded products and extrusion molded products, polymer microparticles are used for modification and improvement of various materials by utilizing the large specific surface area and the structure of microparticles. Their major uses include modifiers for cosmetics, additives for toners, rheology modifiers for paints and the like, agents for medical diagnosis and examination, and additives for molded products such as automobile materials and construction materials.

On the other hand, with interest growing in recent environmental problems, there are increasing demands for using materials of non-petroleum origin to reduce environmental loads, even in the fields where polymer microparticles are used such as cosmetics and paints. Polylactic acid is one of the representative examples of such non-petroleum origin polymers.

As a conventional method of producing polylactic acid-based resin microparticles or powders, there are several known methods: for example, crushing methods (JP-A-2000-007789 and JP-A-2001-288273) typified by freeze crushing method; dissolution-deposition methods (JP-A-2005-002302 and JP-A-2009-242728) in which deposition is performed by being cooled after being dissolved in a solvent at a high temperature, or in which deposition is performed by adding a poor solvent after being dissolved in a solvent; and melt-kneading methods (JP-A-2004-269865 and JP-A-2005-200663) in which a resin compound containing both a polylactic acid-based resin in dispersed phase and an incompatible resin in continuous phase is formed by kneading the polylactic acid-based resin together with the incompatible resin in a kneading machine such as a two-axis extruder, and in which the incompatible resin is removed subsequently to produce polylactic acid-based resin microparticles.

However, the polylactic acid-based resin microparticles produced by the above-described methods have several problems in that the particles produced are not spherical in shape, particle diameter does not become smaller, particle diameter distribution is broad and, in some cases, it is impossible to keep the particles in a round shape because of fiber-shaped ones or the like. Particularly, in the fields such as cosmetics where great importance is attached to feeling of touch and impression, or in the fields such as paints where it is important to control rheology, effects produced by adding such microparticles were not sufficient hitherto.

On the other hand, as a method for production of polymer microparticles, the method described in WO 2009-142231 is known as a method utilizing emulsion. However, in WO '231, a concrete example of polylactic acid-based resin is not disclosed and it is not clear how to produce polylactic acid-based resin microparticles.

It could therefore be helpful to provide a process of producing polylactic acid-based resin microparticles, porous polylactic acid-based resin microparticles which have small average particle diameter and high oil absorption ability and are appropriately usable for cosmetics and the like, and smooth surface polylactic acid-based resin microparticles which have spherical shape and narrow particle diameter distribution and are appropriately usable for toners and the like.

SUMMARY

We thus provide:
(1) A process for producing polylactic acid-based resin microparticles comprising:
a dissolving process for forming a system, which can cause phase separation into two phases of a solution phase mainly composed of polylactic acid-based resin (A) and a solution phase mainly composed of polymer (B) different from polylactic acid-based resin, by dissolving the polylactic acid-based resin (A) and the polymer (B) different from polylactic acid-based resin in ether-based organic solvent (C);
an emulsion-forming process for forming an emulsion by applying a shear force to the system; and
a microparticle-forming process for precipitating polylactic acid-based resin microparticles by bringing the emulsion into contact with a poor solvent which has lower solubility of the polylactic acid-based resin (A) than the ether-based organic solvent (C).
(2) The process for producing polylactic acid-based resin microparticles according to (1), wherein the ether-based organic solvent (C) has a boiling point of 100° C. or higher.
(3) The process for producing polylactic acid-based resin microparticles according to (2), wherein the ether-based organic solvent (C) is diethylene glycol dimethyl ether.
(4) The process for producing polylactic acid-based resin microparticles according to any of (1) to (3), wherein the polymer different from a polylactic acid-based resin (B) is a polyvinyl alcohol, a hydroxypropyl cellulose, a polyethylene oxide or a polyethylene glycol.
(5) The process for producing polylactic acid-based resin microparticles according to any of (1) to (4), wherein the poor solvent is water.
(6) The process for producing polylactic acid-based resin microparticles according to any of (1) to (5), wherein the polylactic acid-based resin (A) has an enthalpy of fusion of 5 J/g or greater.
(7) The process for producing polylactic acid-based resin microparticles according to (6), wherein contact temperature of the poor solvent is equal to or higher than crystallization temperature of the polylactic acid-based resin (A).
(8) The process for producing polylactic acid-based resin microparticles according to any of (1) to (5), wherein the polylactic acid-based resin (A) has an enthalpy of fusion of less than 5 J/g.
(9) Polylactic acid-based resin microparticles characterized in that the microparticles have a number average particle diameter of 1 to 90 μm and a linseed oil absorption of 90 ml/100 g or greater.
(10) The polylactic acid-based resin microparticles according to (9), wherein the microparticles comprise a polylactic acid-based resin having an enthalpy of fusion of at least 5 J/g.
(11) The polylactic acid-based resin microparticles according to (9) or (10), wherein the microparticles have a particle diameter distribution index of 1 to 2.
(12) Polylactic acid-based resin microparticles characterized in that the microparticles have a sphericity of at least 90 and a particle diameter distribution index of 1 to 2.

(13) The polylactic acid-based resin microparticles according to (12), wherein the microparticles comprise a polylactic acid-based resin having an enthalpy of fusion of less than 5 J/g.

(14) The polylactic acid-based resin microparticles according to (12) or (13), wherein the microparticles have a number average particle diameter of 1 to 100 μm and a linseed oil absorption of less than 70 ml/100 g.

(15) Cosmetics which comprise the polylactic acid-based resin microparticles according to any of 9 to 14.

According to the process of producing polylactic acid-based resin microparticles, it becomes possible to produce polylactic acid-based microparticles easily and, further, it becomes possible to produce desired polylactic acid-based resin microparticles as required, for example, porous polylactic acid-based resin microparticles having excellent oil absorption ability and having excellent hygroscopic property, or spherical polylactic acid-based resin microparticles having smooth surface and having high slidability. The polylactic acid-based resin microparticles are suitable for various uses such as cosmetic foundation, lipsticks, cosmetic material such as scrub agent for men's cosmetics, flash-moldable material, rapid prototyping/rapid manufacturing material, paste resin for plastic sol, powder blocking agent, powder flowability improving agent, adhesive, lubricant, rubber compounding ingredient, polishing agent, viscosity improver, filter material/filter aid, gelatinizer, coagulation agent, additive for paints, oil absorbing material, mold releasing agent, slippage improving agent for plastic films/sheets, antiblocking agent, gloss adjusting agent, frosted finish agent, light diffusion agent, surface hardness improving agent, various other modifying agents such as toughness improving material, spacer for liquid crystal display equipment, filler/carrier for chromatography, base material/additive for cosmetic foundation, assistant for micro-capsules, medical materials for drug delivery system/diagnostic reagents, support agent for perfume/pesticide, catalyst/carrier for chemical reactions, gas adsorption agent, sintered material for ceramic processing, standard particle material for measurement/analysis, particle material for food manufacture industry, material for powder coating, and toner for electrophotographic development.

DETAILED DESCRIPTION

Figure 1:
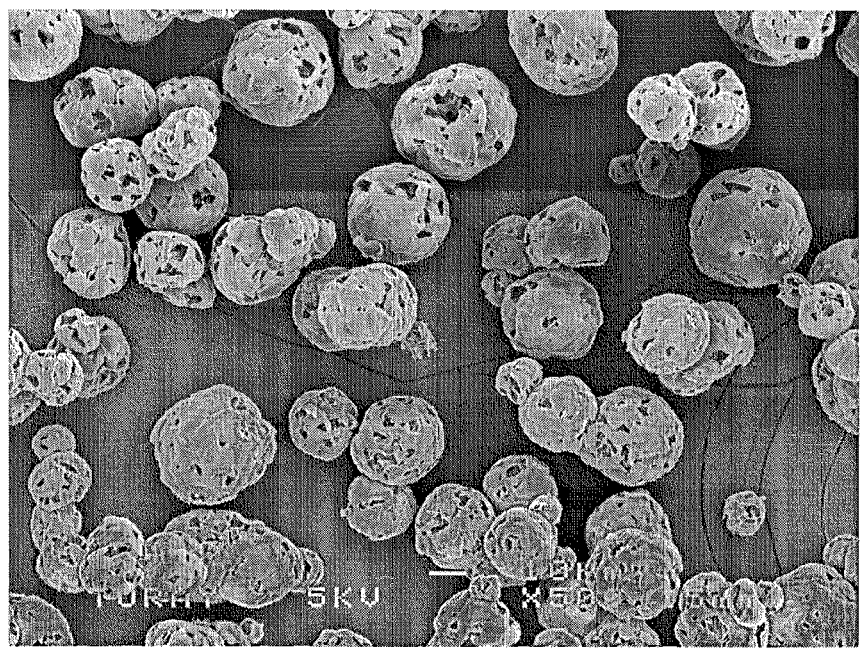
FIG. 1 is an observation diagram by a scanning electron microscope, showing polylactic acid-based resin microparticles produced in Practical Example 2.

The process of producing polylactic acid-based resin microparticles is characterized by having: a dissolving process for forming a system, which can cause phase separation into two phases of a solution phase mainly composed of polylactic acid-based resin (A) and a solution phase mainly composed of polymer (B) different from polylactic acid-based resin, by dissolving the polylactic acid-based resin (A) and the polymer (B) different from polylactic acid-based resin in ether-based organic solvent (C); an emulsion-forming process for forming an emulsion by applying a shear force to the system; and a microparticle-forming process for precipitating polylactic acid-based resin microparticles by bringing the emulsion into contact with a poor solvent which has lower solubility of the polylactic acid-based resin (A) than the ether-based organic solvent (C).

The process of producing polylactic acid-based resin microparticles is characterized in that the organic solvent used is an ether-based organic solvent (C). By using an ether-based organic solvent (C), it becomes possible to prevent polylactic acid-based resin microparticles from fusing together when bringing a poor solvent of polylactic acid-based resin (A) into contact. In the case of using an organic solvent different from the ether-based organic solvent (C), for example, an ester-based solvent such as ethyl acetate and methyl acetate, an alkyl halide-based solvent such as chloroform, bromoform, methylene chloride, 1,2-dichloroethane, 1,1,1-trichloroethane, chlorobenzene and 2,6-dichlorotoluene, a ketone-based solvent such as acetone, methyl ethyl ketone, methyl isobutyl ketone and methyl butyl ketone, an acetal-based solvent such as dimethyl acetal, diethyl acetal, dipropyl acetal and dioxolane, aprotic solvent such as N-methyl-2-pyrrolidone, dimethyl sulfoxide, N,N-dimethyl formamide, N,N-dimethyl acetamide, propylene carbonate, trimethyl phosphate, 1,3-dimethyl-2-imidazolidinone and sulfolane, or a carboxylic acid-based solvent such as formic acid, acetic acid, propionic acid, butyric acid and lactic acid, owing to a good solubility of polylactic acid-based resin, the performance of precipitation of polylactic acid-based resin is not sufficient and it is difficult to form particles. Furthermore, when bringing a poor solvent of polylactic acid-based resin into contact, the solvent remains inside the polylactic acid-based resin microparticles precipitated, polylactic acid-based resin microparticles are liable to fuse with each other, and it increases the possibility of a negative effect on the shape of particles and the particle diameter distribution.

Practically, representative ether-based organic solvents (C) described above include linear aliphatic ethers such as diethyl ether, dipropyl ether, diisopropyl ether, dibutyl ether, dipentyl ether, dihexyl ether, dioctyl ether, diisoamyl ether, tert-amyl methyl ether, tert-butyl ethyl ether, butyl methyl ether, butyl ethyl ether, 1-methoxy ethane (monoglyme), 1-ethoxyethane, diethylene glycol dimethyl ether (diglyme), ethylene glycol diethyl ether, 2-methoxy ethyl ether, di(ethylene glycol) diethyl ether, di(ethylene glycol) dibutyl ether and triethylene glycol dimethyl ether, cyclic aliphatic ethers such as tetrahydrofuran, 2-methyl tetrahydrofuran, 2,5-dimethyl tetrahydrofuran, 2,2,5,5-tetramethylhydrofuran, 2,3-dihydro-furan, 2,5-dihydro-furan, tetrahydropyran, 3-methyl tetrahydropyran and 1,4-dioxane, and aromatic ethers such as anisole, phenetole (ethylphenol), diphenyl ether, 3-phenoxytoluene, p-tolyl ether, 1,3-diphenoxybenzene and 1,2-diphenoxyethane. Particularly, from the viewpoint of industrial availability, dipropyl ether, diisopropyl ether, dibutyl ether, 1-ethoxyethane, diethylene glycol dimethyl ether (diglyme), ethylene glycol diethyl ether, 2-methoxyethyl ether, di(ethylene glycol) diethyl ether, tetrahydrofuran, 2-methyl tetrahydrofuran, tetrahydropyran, 1,4-dioxane and anisole are preferred.

Further, from the viewpoint of simplifying the process in which the ether-based organic solvent (C) is recycled by removing the poor solvent of polylactic acid-based resin from the ether-based organic solvent (C) and the polymer (B) different from polylactic acid-based resin separated in an solid-liquid separating process when producing the above-described microparticles of polylactic acid-based resin, it is preferred that the above-described ether-based organic solvent has a boiling point of 100 degrees Celsius or higher. For such an ether-based organic solvent, for example, diethylene glycol dimethyl ether (diglyme) and 1,4-dioxane can be used. Such an ether-based organic solvent can be used either singly or in mixture, however, from the viewpoint of simplifying the process for recycling the ether-based organic solvent, it is preferred to be used singly.

Furthermore, other organic solvents can be added to the ether-based organic solvent (C) as long as the desired effect is not spoiled. If the amount of ether-based organic solvent is 100 parts by mass, the amount of other organic solvents added are generally less than 100 parts by mass, preferably 75 parts by mass or less, more preferably 50 parts by mass or less, still more preferably 30 parts by mass or less, particularly preferably 20 parts by mass or less, and most preferably 10 parts by mass or less. Typical examples of the other organic solvents include ester-based solvents such as ethyl acetate and methyl acetate, alkyl halide-based solvents such as chloroform, bromoform, methylene chloride, 1,2-dichloroethane, 1,1,1-trichloroethane, chlorobenzene and 2,6-dichlorotoluene, ketone-based solvents such as acetone, methyl ethyl ketone, methyl isobutyl ketone and methyl butyl ketone, acetal-based solvents such as dimethyl acetal, diethyl acetal, dipropyl acetal and dioxolane, aprotic solvents such as N-methyl-2-pyrrolidone, dimethyl sulfoxide, N,N-dimethyl formamide, N,N-dimethyl acetamide, propylene carbonate, trimethyl phosphate, 1,3-dimethyl-2-imidazolidinone and sulfolane, and carboxylic acid-based solvents such as formic acid, acetic acid, propionic acid, butyric acid and lactic acid. These other organic solvents can be used either singly or in mixture.

The above-described polylactic acid-based resin (A) is a polymer in which main components are L-lactic acid and D-lactic acid. "A polymer in which main components are L-lactic acid and D-lactic acid" means that, in the monomer units constituting copolymers in the polylactic acid-based resin (A), the total of the monomer units of L-lactic acid and D-lactic acid are 50 mole % or more in the molar ratio. The molar ratio of the total of the monomer units of L-lactic acid and D-lactic acid is preferably 50 mole % or more, more preferably 70 mole % or more, further more preferably 80 mole % or more, particularly preferably 90 mole % or more. The upper limit is generally 100 mole %.

"L" and "D" refer to kinds of optical isomers. The lactic acid having a native type configuration is described as "L-lactic acid" or "L-type lactic acid," and the lactic acid having a non-native type configuration is described as "D-lactic acid" or "D-type lactic acid."

In the above-described polylactic acid-based resin (A), the arrangement of lactic acid monomer units is not particularly limited and may be any of a block copolymer, an alternating copolymer, a random copolymer and a graft copolymer. From the viewpoint of lowering a fusing temperature, the random copolymer is preferable.

Another characteristic is that wide variety of polylactic acid-based resin (A) from crystalline ones to amorphous ones can be used to produce polylactic acid-based resin microparticles, and that it is possible to control the shape of polylactic acid-based resin microparticles by selecting either crystalline or amorphous polylactic acid-based resin (A).

When polylactic acid-based resin (A) has high crystallization characteristics, it becomes possible to produce porous polylactic acid-based resin microparticles. The crystallization characteristics of the polylactic acid-based resin (A) can be expressed in enthalpy of fusion. The higher enthalpy of fusion indicates the higher crystal characteristics, and the lower enthalpy of fusion indicates that the polylactic acid-based resin is more amorphous.

When enthalpy of fusion of the polylactic acid-based resin (A) is 5 J/g or more, the crystallization characteristics of the polylactic acid-based resin (A) become high and polylactic acid-based resin microparticles having a porous surface can be obtained. When the crystallization characteristics of the polylactic acid-based resin (A) become higher, polylactic acid-based resin microparticles in more porous shape can be obtained and properties taking advantage of porous structure such as oil absorption property and hygroscopic property of the polylactic acid-based resin microparticles improve. Therefore, when producing polylactic acid-based resin microparticles having a porous surface, the lower limit of enthalpy of fusion is preferably 10 J/g or more, more preferably 20 J/g or more, and most preferably 30 J/g or more. Further, the upper limit is preferably 100 J/g or less, although it is not limited in particular.

On the other hand, in the case where the polylactic acid-based resin (A) is amorphous, it is possible to produce polylactic acid-based resin microparticles having a smooth surface. Although the tangible reason is unclear, in the case where the polylactic acid-based resin (A) precipitates in an amorphous state, presumably because of inhibition of partial crystallization, the particles precipitate in an homogeneous state and the surface of those becomes smooth.

When producing polylactic acid-based resin microparticles having a smooth surface, the less enthalpy of fusion the polylactic acid-based resin (A) has, the more likely the precipitation occurs in a homogeneous state. Therefore, the upper limit of enthalpy of fusion is preferably less than 5 J/g, more preferably less than 3 J/g, further more preferably less than 2 J/g, and most preferably less than 1 J/g. Further, the lower limit is 0 J/g, and it indicates that the polylactic acid-based resin (A) is completely in an amorphous state.

Enthalpy of fusion refers to a value calculated from a peak area, which shows heat capacity of fusion at approximately 160 degrees Celsius, in a differential scanning calorimetry (DSC) where a temperature is raised to 200 degrees Celsius with the temperature rise of 20 degrees Celsius per minute.

As for a method of regulating enthalpy of fusion, it is possible to use known methods such as a method of controlling co-polymerization ratio (L/D) between L-lactic acid and D-lactic acid which constitute the polylactic acid-based resin (A), a method of adding an additive agent for promoting crystallization to the polylactic acid-based resin (A), and a method of forming a stereo block structure. Above all, due to its easiness of controlling enthalpy of fusion of the polylactic acid-based resin (A), the method of controlling co-polymerization ratio of L/D is preferred. When L/D ratio is 95/5 or more, enthalpy of fusion becomes 5 J/g or more and the polylactic acid-based resin becomes crystalline. It is preferred that the co-polymerization ratio of L-lactic acid is high because higher ratio facilitates crystallization. L/D is more preferably 97/3 or more, and most preferably 98/2 or more. The upper limit of L/D is less than 100/0. Further, when L/D is less than 95/5, enthalpy of fusion becomes less than 5 J/g and the polylactic acid-based resin becomes amorphous. It is preferred that the co-polymerization ratio of L-lactic acid is low because lower ratio facilitates being amorphous. The ratio is more preferably less than 92/8 and most preferably less than 89/11. Further, the lower limit of L/D is 50/50 or more. Because optical isomers such as L and D are materials in which molecule structures are mirror images of each other and physical properties are not different, enthalpy of fusion remains unchanged when the above-described L/D is substituted with D/L and consequently our process also includes the extent where L/D is substituted with D/L.

Further, the polylactic acid-based resin (A) may contain copolymerization ingredients other than lactic acid as long as the desired effect is not spoiled. The other copolymerization ingredient units can be, for example, a multivalent carboxylic acid, a polyhydric alcohol, a hydroxycarboxylic acid or a lactone and, specifically, can be multivalent carboxylic acids such as oxalic acid, malonic acid, succinic acid, glutaric acid, adipic acid, azelaic acid, sebacic acid, dodecanedioic acid, fumaric acid, cyclohexanedicarboxylic acid, terephthalic acid, isophthalic acid, phthalic acid, 2,6-naphthalenedicarboxylic acid, anthracene dicarboxylic acid, 5-sodium sulfoisophthalic acid and 5-tetrabutyl phosphonium sulfoisophthalic acid; polyhydric alcohols such as ethylene glycol, propylene glycol, butanediol, heptanediol, hexanediol, octanediol, nonanediol, decanediol, 1,4-cyclohexanedimethanol, neopentylglycol, glycerin, pentaerythritol, bisphenol A, an aromatic polyhydric alcohol produced by an addition reaction of ethylene oxide to a bisphenol, diethylene glycol, triethylene glycol, polyethylene glycol, polypropylene glycol and polytetramethylene glycol; hydroxycarboxylic acids such as glycolic acid, 3-hydroxybutyric acid, 4-hydroxybutyric acid, 4-hydroxyvaleric acid, 6-hydroxycaproic acid and hydroxybenzoic acid; or lactones such as glycolide, ε-caprolactone glycolide, ε-caprolactone, β-propiolactone, δ-butyrolactone, β-butyrolactone, γ-butyrolactone, pivalolactone and δ-valerolactone. The volume content of the other copolymerization units is preferably 30 mol % or less, more preferably 20 mol % or less, further more preferably 10 mol % or less, most preferably 5 mol % or less, relative to the total monomer units of polylactic acid-based resin (A) as 100 mol %.

Although molecular mass and molecular mass distribution of the polylactic acid-based resin (A) are not limited in particular as far as it can be dissolved in the ether-based organic solvent (C) substantially, from the viewpoint of ease of keeping particle structure and of improvement of hydrolysis resistance, the lower limit of weight average molecular mass of the polylactic acid-based resin (A) is preferably 10,000 or more, more preferably 50,000 or more, further more preferably 100,000 or more, most preferably 200,000 or more. Further, although not limited in particular, the upper limit of weight average molecular mass is preferably 1,000,000 or less. The weight average molecular mass referred to herein is weight average molecular mass in terms of polymethyl methacrylate (PMMA), measured in gel permeation chromatography (GPC) using hexafluoroisopropanol as a solvent.

For production of the polylactic acid-based resin (A), it is not limited particularly and known methods can be used such as direct polymerization from polylactic acid and ring-opening polymerization via a lactide.

The above-described polymer (B) different from polylactic acid-based resin may include a thermoplastic resin and a thermosetting resin, however, in view of better solubility in the ether-based organic solvent (C), thermoplastic resin is preferred.

More specifically, the polymer (B) different from polylactic acid-based resin may include one or more of the following: a synthetic resin such as poly(vinyl alcohol) (may be either a complete saponification type or a partial saponification type of poly(vinyl alcohol)), poly(vinyl alcohol-ethylene) copolymer (may be either a complete saponification type or a partial saponification type of poly(vinyl alcohol-ethylene) copolymer), polyvinylpyrrolidone, poly(ethylene glycol), poly(ethylene oxide), sucrose fatty acid ester, poly(oxyethylene fatty acid ester), poly(oxyethylene lauric fatty acid ester), poly(oxyethylene glycol mono-fatty acid ester), poly(oxyethylene alkyl phenyl ether), poly(oxyalkylether), polyacrylic acid, sodium polyacrylate, poly(methacrylic acid), sodium polymethacrylate, polystyrene sulfonic acid, polystyrene sodium sulfonate, poly(vinyl pyrrolidinium chloride), poly(styrene-maleic acid) copolymer, aminopoly(acrylic amide), poly-p-vinylphenol, polyarylamine, polyvinyl ether, polyvinyl formal, poly(acrylic amide), poly(methacrylamide), poly(oxyethyleneamine), poly(vinyl pyrrolidone), poly(vinyl pyridine), polyaminosulfone and polyethyleneimine, disaccharides such as maltose, cellobiose, lactose and sucrose; cellulose derivatives such as cellulose, chitosan, hydroxyethyl cellulose, hydroxypropyl cellulose, methylcellulose, ethyl cellulose, ethyl hydroxy cellulose, carboxymethylethylcellulose, carboxymethylcellulose, sodium carboxymethylcellulose and cellulose ester; polysaccharides and their derivatives such as amylose and its derivatives, starch and its derivatives, dextrin, cyclodextrin, sodium alginate and its derivatives; gelatin, casein, collagen, albumin, fibroin, keratin, fibrin, carrageenan, chondroitin sulfate, arabian gum, agar and protein; and from the viewpoint of narrowing the particle diameter distribution, preferably includes one or more of the following: poly(vinyl alcohol) (may be either a complete saponification type or a partial saponification type of poly(vinyl alcohol)), poly(vinyl alcohol-ethylene) (may be either a complete saponification type or a partial saponification type of poly(vinyl alcohol-ethylene)), poly(ethyleneglycol), poly(ethyleneoxide), sucrose fatty acid ester, poly(oxyethylene alkyl phenyl ether), poly(oxyethylene alkyl phenyl ether), polyacrylic acid, poly(methacrylic acid), carboxymethylcellulose, hydroxyethyl cellulose, hydroxypropyl cellulose, methyl cellulose, ethyl cellulose, ethyl hydroxy cellulose, carboxymethylethylcellulose, carboxymethylcellulose, sodium carboxymethylcellulose, cellulose derivatives such as cellulose ester, and polyvinylpyrrolidone; more preferably includes one or more of the following: poly(vinyl alcohol) (may be either a complete saponification type or a partial saponification type of poly(vinyl alcohol)), poly(vinyl alcohol-ethylene) (may be either a complete saponification type or a partial saponification type of poly(vinyl alcohol-ethylene)), poly(ethylene glycol), poly(ethylene oxide), carboxymethylcellulose, hydroxyethyl cellulose, hydroxypropyl cellulose, methyl cellulose, ethyl cellulose, ethyl hydroxy cellulose, carboxymethylethylcellulose, carboxymethylcellulose, sodium carboxymethylcellulose, cellulose derivatives such as cellulose ester, and polyvinylpyrrolidone; particularly preferably includes one or more of the followings: poly(vinyl alcohol) (may be either a complete saponification type or a partial saponification type of poly(vinyl alcohol)), poly(ethylene glycol), poly(ethylene oxide), and hydroxypropyl cellulose.

The molecular mass of the polymer (B) different from polylactic acid-based resin is preferably in a range of 1,000-100,000,000, more preferably in a range of 1,000-10,000,000, further more preferably in a range of 5,000-1,000,000, particularly preferably in a range of 10,000-500,000, most preferably in a range of 10,000-100,000, in terms of weight average molecular mass.

The weight average molecular mass referred to herein denotes a weight average molecular mass measured in terms of polyethylene glycol by gel permeation chromatography (GPC) using water as a solvent. In the case where water cannot be used for the measurement, dimethylformamide is used as a solvent and, if the measurement cannot be performed, tetrahydrofuran will be used. In case the measurement is still impossible, hexafluoroisopropanol will be used.

The above-described "a system, which can cause phase separation into two phases of a solution phase mainly composed of polylactic acid-based resin (A) and a solution phase mainly composed of polymer (B) different from polylactic acid-based resin, by dissolving the polylactic acid-based resin (A) and the polymer (B) different from polylactic acid-based resin in ether-based organic solvent (C)" denotes a system comprising a solution in which the polylactic acid-based resin (A) and the polymer (B) different from polylactic acid-based resin are dissolved in the ether-based organic solvent (C) and being capable of phase separation into two phases of a solution phase mainly composed of the polylactic acid-based resin (A) and a solution phase mainly composed of the polymer (B) different from polylactic acid-based resin.

By using such a system capable of phase separation, it is possible to emulsify the system by mixing it under the condition of phase separation and consequently to form an emulsion.

In the description above, whether the polymers can be dissolved or not is determined by dissolving the polylactic acid-based resin (A) and the polymer (B) different from polylactic acid-based resin in the ether-based organic solvent (C) and checking whether the polymers can be dissolved in the ether-based organic solvent (C) by 1 mass % or more, at a temperature at which the phase separation is caused.

In this emulsion, the solution phase of polylactic acid-based resin (A) becomes a dispersed phase and the solution phase of polymer B becomes a continuous phase. Further, by bringing a poor solvent of polylactic acid-based resin (A) into contact with the emulsion, polylactic acid-based resin microparticles are precipitated out of the solution phase of polylactic acid-based resin (A) in the emulsion and consequently polymer microparticles consisting of polylactic acid-based resin (A) can be obtained.

The poor solvent of polylactic acid-based resin (A) refers to a solvent having a lower solubility of polylactic acid-based resin (A) than the above-described ether-based organic solvent (C) and being hardly capable of dissolving polylactic acid-based resin (A) and, more specifically, refers to a solvent in which the solubility of polylactic acid-based resin (A) is 1 mass % or less. The upper limit of the solubility of polylactic acid-based resin (A) in the poor solvent is more preferably 0.5 mass % or less, further more preferably 0.1 mass % or less.

In the above-described production process, the poor solvent of polylactic acid-based resin (A) used is preferably a poor solvent of polylactic acid-based resin (A) which can dissolve polymer (B) different from polylactic acid-based resin. By using this, it becomes possible to precipitate polylactic acid-based resin microparticles consisting of polylactic acid-based resin (A) efficiently. Further, the poor solvent of polylactic acid-based resin (A) is preferably a solvent which can mix homogeneously with a solvent capable of dissolving both polylactic acid-based resin (A) and polymer (B) different from polylactic acid-based resin.

As regards the poor solvent described above, an optimally suited one can be selected as appropriate in accordance with the type of polylactic acid-based resin (A), preferably with the type of polylactic acid-based resin (A) and the type of polymer (B) different from polylactic acid-based resin. More specifically, it may include one or more solvents selected from the group consisting of the followings: an aliphatic hydrocarbon-based solvent such as pentane, hexane, heptane, octane, nonane, n-decane, n-dodecane, n-tridecane, cyclohexane and cyclopentane; an aromatic hydrocarbon-based solvent such as benzene, toluene and xylene; an alcohol-based solvent such as methanol, ethanol, 1-propanol and 2-propanol; and water. From the viewpoint of efficient precipitation of polylactic acid-based resin (A), the poor solvent of polylactic acid-based resin is preferably an aliphatic hydrocarbon-based solvent, an aromatic hydrocarbon-based solvent, an alcohol-based solvent or water, more preferably an alcohol-based solvent or water, most preferably water.

By selecting the above-described polylactic acid-based resin (A), polymer (B) different from polylactic acid-based resin, ether-based organic solvent (C) capable of dissolving those and utilizing those in combination, it becomes possible to precipitate polylactic acid-based resin efficiently and consequently to obtain polymer microparticles.

It is necessary that a liquid in which polylactic acid-based resin (A), polymer (B) different from polylactic acid-based resin and ether-based organic solvent (C) capable of dissolving those are dissolved and mixed can cause phase separation into two phases of a solution phase mainly composed of the polylactic acid-based resin (A) and a solution phase mainly composed of the polymer (B) different from polylactic acid-based resin. The two ether-based organic solvent (C), one solvent is in the solution phase mainly composed of polylactic acid-based resin (A) and the other solvent is in the solution phase mainly composed of polymer (B) different from polylactic acid-based resin, may be identical with or may be different from each other. However, it is preferred that these solvents are substantially identical.

The condition causing two phase separation varies according to the types of polylactic acid-based resin (A) and polymer (B) different from polylactic acid-based resin, the molecular masses of polylactic acid-based resin (A) and polymer (B) different from polylactic acid-based resin, the type of ether-based organic solvent (C), the concentrations of polylactic acid-based resin (A) and polymer (B) different from polylactic acid-based resin, and the temperature and pressure to carry out our process.

To meet conditions under which the phase separation is likely to occur, it is preferred that there is a significant difference in solubility parameter (hereinafter, may also be referred to as SP value) between the polylactic acid-based resin (A) and the polymer (B) different from polylactic acid-based resin.

Preferably, the lower limit of the difference between the SP values is 1 $(J/cm^3)^{1/2}$ or more, more preferably 2 $(J/cm^3)^{1/2}$ or more, still more preferably 3 $(J/cm^3)^{1/2}$ or more, particularly preferably 5 $(J/cm^3)^{1/2}$ or more, and most preferably 8 $(J/cm^3)^{1/2}$ or more. When the SP values are in this range, the phase separation tends to occur easily, and the tendency to the phase separation makes it possible to produce polylactic acid-based resin microparticles containing more polylactic acid-based resin ingredients. The upper limit of the difference of the SP values is preferably 20 $(J/cm^3)^{1/2}$ or less, more preferably 15 $(J/cm^3)^{1/2}$ or less, further more preferably 10 $(J/cm^3)^{1/2}$ or less. However, it is not particularly limited thereto as long as both polylactic acid-based resin (A) and polymer (B) different from polylactic acid-based resin can be dissolved in ether-based organic solvent (C). The SP value referred to herein is calculated in accordance with Fedor's estimation method (hereinafter, may also be referred to as Computational method) which is a calculation method based on coagulation energy density and molar molecular mass (Hideki YAMAMOTO, "THE BASIS, APPLICATION AND CALCULATION METHOD OF SP VALUE," Johokiko Co., Ltd., published at 31 Mar. 1999). Further, in the case where the above-described calculation method cannot be used, the solubility parameter which is determined by experiment on the basis of whether it can be dissolved in a known solvent or not (hereinafter, may also be referred to as Experimental method) is used as a substitute for the SP value (J. Brand, "POLYMER HANDBOOK FOURTH EDITION," Wiley, published in 1998).

To determine appropriate conditions under which the phase separation occurs, it is possible to utilize a three-component phase diagram which can be prepared by a simple preliminary test of observing state changes by varying the ratio among three components, namely, polylactic acid-based resin (A), polymer (B) different from polylactic acid-based resin and ether-based organic solvent (C) in which those are dissolved.

The phase diagram is prepared by evaluating whether an interface is formed among phases or not when polylactic acid-based resin (A), polymer (B) different from polylactic acid-based resin and ether-based organic solvent (C) are mixed at an arbitrary ratio, dissolved together and left still for a certain period of time. To prepare the diagram, the evaluations are performed under at least three different conditions, preferably at least five different conditions, more preferably at least ten different conditions. By distinguishing between a region of two-phase separation and a region of single phase according to the phase diagram which can be prepared as described above, it becomes possible to determine conditions under which the phase separation occurs.

To determine whether the phase separation occurs or not, after the volumes of polylactic acid-based resin (A), polymer (B) different from polylactic acid-based resin and ether-based organic solvent (C) are tuned to an arbitrary ratio, polylactic acid-based resin (A) and polymer (B) different from polylactic acid-based resin are dissolved in ether-based organic solvent (C) completely and are stirred sufficiently, under certain temperature and pressure conditions where the dissolving process will be performed. Then, after keeping them still for three days, it is examined macroscopically whether the phase separation occurs or not. However, in the case where the emulsion becomes stable considerably, the phase separation does not occur even after keeping them still for three days. In such cases, the presence or absence of the phase separation is determined on the basis of whether the phase separation can be observed microscopically or not by using an optical microscope, a phase-contrast microscope or the like.

The phase separation occurs as a result of the separation of polylactic acid solution phase mainly composed of polylactic acid-based resin (A) and polymer B solution phase mainly composed of polymer (B) different from polylactic acid-based resin in ether-based organic solvent (C). The solution phase of polylactic acid-based resin (A) is a phase in which polylactic acid-based resin (A) is mainly distributed, and the polymer B solution phase is a phase in which polymer (B) different from polylactic acid-based resin is mainly distributed. In this case, it is presumed that the solution phase of polylactic acid-based resin (A) and the polymer B solution phase have a volume ratio varying with types and amounts of polylactic acid-based resin (A) and polymer (B) different from polylactic acid-based resin.

As an industrially feasible concentration where the phase separation occurs, both concentrations of polylactic acid-based resin (A) and polymer (B) different from polylactic acid-based resin in ether-based organic solvent are not particularly limited as long as the concentrations are within a range of being dissolved in ether-based organic solvent. From the viewpoint of causing phase separation and of industrially feasible concentration, the lower limit of each of concentrations is preferably more than 1 mass %, more preferably 2 mass %, further more preferably 3 mass %, further more preferably 5 mass %, relative to the total amount of mass. Further, the upper limit of each of the concentrations is preferably 50 mass %, more preferably 30 mass %, further more preferably 20 mass %.

It is presumed that, as regards the above-described two phases of the solution phase of polylactic acid-based resin (A) and the polymer B solution phase, the interface tension between two phases becomes small because both phases are organic solvents and, as a result, the emulsion generated is stabilized and the particle diameter distribution becomes narrow.

The interfacial tension between the two phases described above is too small to measure directly with the commonly-used pendant-drop method in which a solution is added to another kind of solution to take measurements. The interfacial tension, however, can be estimated from the surface tension of each phase exposed to air. Thus, assuming r1 and r2 represent the surface tension of each phase exposed to air, the interfacial tension r12 is estimated to be the absolute value of the difference between them as follows: r12=|r1−r2| (the absolute value of r1−r2).

As regards the preferred range of r12, the upper limit is preferably 10 mN/m, more preferably 5 mN/m, further more preferably 3 mN/m, and particularly preferably 2 mN/m. Further, the lower limit is more than 0 mN/m.

The viscosity ratio between the two phases influences the average particle diameter and the particle diameter distribution, and the particle diameter distribution tends to decrease with a decreasing viscosity ratio.

As regards the preferred range of the viscosity ratio between the two phases described above, the lower limit is preferably 0.1 or more, more preferably 0.2 or more, further more preferably 0.3 or more, particularly preferably 0.5 or more, remarkably preferably 0.8 or more. Further, the upper limit is preferably 10 or less, more preferably 5 or less, further more preferably 3 or less, particularly preferably 1.5 or less, remarkably preferably 1.2 or less. The viscosity ratio between two phases referred to herein is defined as "a viscosity of the solution phase of polylactic acid-based resin (A)/a viscosity of the solution phase of polymer (B) different from polylactic acid-based resin" at a temperature at which the dissolution process will be performed.

By using the system which can cause phase separation, polymer microparticles are produced after a phase separated liquid phase is mixed to be emulsified.

To form microparticles, the emulsion-forming process and the microparticle-forming process can be carried out in a common reaction vessel. As regards a temperature to carry out the emulsion-forming process and the microparticle-forming process, from the viewpoint of industrial feasibility, the lower limit is generally 0 degrees Celsius or higher, preferably 10 degrees Celsius or higher, more preferably 20 degrees Celsius or higher. Further, the upper limit is preferably 300 degrees Celsius or lower, more preferably 200 degrees Celsius or lower, further more preferably 160 degrees Celsius or lower, particularly preferably 140 degrees Celsius or lower, remarkably preferably 100 degrees Celsius or lower, although it is not particularly limited as long as the temperature is in a range where polylactic acid-based resin (A) and polymer (B) different from polylactic acid-based resin can be dissolved to cause phase separation so that the desired microparticles can be produced.

From the viewpoint of industrial feasibility, when carrying out the emulsion-forming process, the pressure is in a range from the standard pressure to 10 atm. The lower limit of the pressure is preferably 1 atm. The upper limit of the pressure is preferably 5 atm, more preferably 3 atm, further more preferably 2 atm.

Further, it is preferred to use an inert gas in the reaction vessel. The inert gas includes, more specifically, nitrogen, helium, argon and carbon dioxide, and preferably includes nitrogen and argon.

Emulsion is formed by mixing the phase separation system described above under such conditions. In other words, emulsion is formed by applying a shear force to a solution which is the phase separation system obtained from the dissolution process described above.

In a process of forming an emulsion, an emulsion is formed such that the solution phase of polylactic acid-based resin (A) forms into particle-like droplets. Generally, in a phase separation, such an emulsion tends to be formed when the volume of the solution phase of polymer (B) different from polylactic acid-based resin is larger than the volume of the solution phase of polylactic acid-based resin (A). In particular, the volume ratio of the solution phase of polylactic acid-based resin (A) is preferably less than 0.5, more preferably in a range of 0.4 to 0.1, relative to the total volume of two phases as 1.

It is possible to define an appropriate range of the volume ratio by measuring the volume ratio and concentration of each component simultaneously when preparing the above-described phase diagram.

The microparticles produced by the present production process have a narrow particle diameter distribution because a remarkably homogeneous emulsion is produced in a stage of forming the emulsion. This tendency becomes apparent when using a single solvent which can dissolve both polylactic acid-based resin (A) and polymer (B) different from polylactic acid-based resin. Thus, to obtain a sufficient shear force for forming the emulsion in the present production process, it is possible to use generally known methods such as liquid phase stirring method by stirring blades, stirring method with a biaxial continuous mixer, mixing method with a homogenizer, and ultrasonic irradiation method.

Particularly, in the case where stirring blades are used, the stirring speed is preferably 50 rpm to 1,200 rpm, more preferably 100 rpm to 1,000 rpm, further more preferably 200 rpm to 800 rpm, particularly preferably 300 rpm to 600 rpm, though the speed is also affected by the shape of the stirring blades.

The stirring blades may have such shapes as propeller, paddle, flat paddle, turbine, double cone, single cone, single ribbon, double ribbon, screw, and helical ribbon, although they are not particularly limited thereto as long as a sufficient shear force can be applied to the system. Further, to perform stirring efficiently, baffle boards and the like may be provided in the reaction vessel.

Furthermore, to produce the emulsion, it is possible to use not only a stirrer but also a generally known device such as an emulsifier and a disperser.

Specific examples include batch type emulsifiers such as Homogenizer (supplied by IKA), Polytron (supplied by Kinematica, Inc.), TK Autohomomixer (supplied by Tokushu Kika Kogyo Co., Ltd.), and others such as Ebara Milder (supplied by Ebara Corporation), T. K. Filmics, T. K. Pipeline Homomixer (supplied by Tokushu Kika Kogyo Co., Ltd.), Colloid Mill (supplied by Shinko-Pantec Co., Ltd.), and Slusher, Trigonal Wet Grinder (Mitsui Miike Kakoki Co., Ltd.), as well as ultrasonic homogenizers and static mixers.

The emulsion thus obtained is subsequently supplied to the microparticle-forming process for precipitating microparticles.

To obtain microparticles of polylactic acid-based resin (A), a poor solvent of polylactic acid-based resin (A) is brought into contact with the emulsion produced by the above-described process and microparticles having a diameter corresponding to the emulsion diameter are produced as a result.

Although the method to bring the poor solvent into contact with the emulsion can be either a method to put the emulsion in the poor solvent or a method to put the poor solvent in the emulsion, the method to put the poor solvent in the emulsion is preferable. For the method of bringing the poor solvent into contact, although both method of putting the emulsion in the poor solvent and method of putting the poor solvent in the emulsion are available, the method of putting the poor solvent in the emulsion is preferable.

For the method of adding the poor solvent, it is not particularly limited as long as desired polymer microparticles can be produced, and any methods such as continuous dropping, split dropping and batch addition can be used. However, to prevent the emulsion from coagulation, fusion and coalescence which can cause widening of particle diameter distribution or generation of bulky grains larger than 1,000 μm while adding the poor solvent, continuous dropping and split dropping are preferable. Further, from the viewpoint of industrially efficient operation, continuous dropping is most preferably used.

For the temperature of bringing the poor solvent into contact, it is not particularly limited as long as it is within a range where polylactic acid-based microparticles can be precipitated. The lower limit thereof is 0 degrees Celsius or higher, and the upper limit is 300 degrees Celsius or lower. The lower limit of the temperature is preferably 10 degrees Celsius or higher, more preferably 20 degrees Celsius or higher, because the poor solvent solidifies and consequently cannot be used if the temperature is too low. Further, the upper limit of the temperature is preferably 200 degrees Celsius or lower, more preferably 100 degrees Celsius or lower, further more preferably 90 degrees Celsius or lower, because polylactic acid-based resin (A) and polymer (B) different from polylactic acid-based resin are prone to become deteriorated by heat if the temperature is too high.

When a crystalline polylactic acid-based resin (A) having enthalpy of fusion of 5 J/g or more is used in the above-described production process, polylactic acid-based resin microparticles having porous forms are produced under normal conditions. However, it is also possible to produce polylactic acid-based resin microparticles having smooth surface by controlling the contact temperature of the poor solvent to a higher temperature than the crystallization temperature of the polylactic acid-based resin (A). Although the tangible reason is unclear, it can be considered that controlling the temperature of the crystalline polylactic acid-based resin (A) to a higher temperature of the crystallization temperature changes the resin into molten amorphous state and consequently smoothes the surface thereof.

The crystallization temperature of polylactic acid-based resin (A) refers to a recrystallization temperature in a process of cooling a molten polylactic acid-based resin. As for the method of measuring the crystallization temperature, a temperature of top peak showing endothermic heat capacity is measured as lowering the temperature at a rate of 1 degree Celsius per minute after raising the temperature to 200 degrees Celsius at a rate of 20 degrees Celsius per minute in a differential scanning calorimetry (DSC). Further, in a case where the peak does not appear while lowering the temperature, it is possible to measure it as a temperature of top peak showing endothermic heat capacity as raising the temperature up to 200 degrees Celsius at a rate of 0.5 degrees Celsius per minute.

When using a crystalline polylactic acid-based resin (A) having enthalpy of fusion of 5 J/g or more, the contact temperature of the poor solvent of producing polylactic acid-based resin microparticles having smooth surfaces is preferably more than the crystallization temperature defined above. Because the polylactic acid-based resin microparticles tend to transform into an amorphous state and tend to have smooth surfaces when the temperature is higher than the crystallization temperature, the lower limit of the temperature is preferably 10 degrees higher than the crystallization temperature, more preferably 20 degrees higher than the crystallization temperature, further more preferably 30 degrees higher than the crystallization temperature. Further, the upper limit of the temperature is preferably 100 degrees higher than the crystallization temperature, although it is not particularly limited thereto.

Further, the time to add the poor solvent is preferably 10 minutes to 50 hours, more preferably 15 minutes to 10 hours, further more preferably 30 minutes to 5 hours. If the time for adding is shorter than those ranges, there is a fear that a widening of the particle diameter distribution or a forming of bulky grains may occur due to coagulation, fusion and coalescence of the emulsion. Further, from the viewpoint of industrial feasibility, it is impractical to spend time longer than those ranges. By carrying out the adding within such a range, it becomes possible to prevent particles from coagulation while transforming the emulsion into polymer particles, and it becomes possible to produce polymer particles having narrow particle diameter distribution as a result.

The quantity of the poor solvent to add depends on a state of the emulsion and is preferably 0.1 to 10 mass part, more preferably 0.1 to 5 mass part, further more preferably 0.2 to 3 mass part, particularly preferably 0.2 to 2 mass part, most preferably 0.2 to 1.0 mass part, relative to the total mass of the emulsion as 1 mass part.

The contact time between the poor solvent and the emulsion is not limited as long as it is sufficient to precipitate microparticles. Although, to cause precipitation sufficiently and achieve high productivity, the contact time is preferably from 5 minutes to 50 hours, more preferably from 5 minutes to 10 hours, further more preferably from 10 minutes to 5 hours, particularly preferably from 20 minutes to 4 hours, most preferably from 30 minutes to 3 hours, after adding the poor solvent.

By separating the thus produced polymer microparticle-dispersed liquid into solids and liquids by a known method such as filtration, vacuum filtration, pressure filtration, centrifugation, centrifugal filtration and spray drying, microparticle powders can be obtained. The polymer microparticles, obtained by the separation into solids and liquids, are purified by removing the adhered or contained impurities by washing with a solvent or the like, as needed.

In the production process described above, the ether-based organic solvent (C) and the polymer (B) different from polylactic acid-based resin, which are separated through the solid-liquid separation process in producing the microparticle powders, can be recycled and utilized once again.

A solvent obtained through the solid-liquid separation is a mixture of polymer (B) different from polylactic acid-based resin, the ether-based organic solvent (C) and the poor solvent. This solvent can be utilized as a solvent for forming an emulsion again by removing the poor solvent therefrom. As a method of removing the poor solvent, known methods can be used such as simple distillation, reduced pressure distillation, precision distillation, thin film distillation, extraction and membrane separation, and simple distillation, reduced pressure distillation or precision distillation is preferably used.

When operating distillation such as simple distillation and reduced pressure distillation, as in the case of producing polymer microparticles, there is a possibility that the system would be heated and that thermal decomposition of polymer (B) different from polylactic acid-based resin and the ether-based organic solvent (C) is promoted as a result. Therefore, the operation is preferably carried out in an oxygen-free atmosphere as much as possible, more preferably in an inert atmosphere. Specifically, it is preferably carried out in an atmosphere of nitrogen, helium, argon or carbon dioxide. Further, antioxidants such as phenol-based compounds or the like can be added thereto.

When carrying out the recycling described above, it is preferred that the poor solvent is removed as much as possible. Specifically, the remaining amount of the poor solvent is generally 10 mass % or less, preferably 5 mass % or less, more preferably 3 mass % or less, particularly preferably 1 mass % or less, relative to the total amount of the recycled, namely, the ether-based organic solvent (C) and the polymer (B) different from polylactic acid-based resin. If the remaining amount of the poor solvent exceeds such a range, there is a fear that the particle diameter distribution of the microparticles widens and the particles coagulate.

The volume of the poor solvent in a solvent used in recycling can be measured by known methods such as gas chromatography and the Karl Fischer method.

In the operation of removing the poor solvent, because there may be a loss of the ether-based organic solvent (C) or polymer (B) different from polylactic acid-based resin practically, it is preferred that the composition ratio is adjusted to the initial ratio as is appropriate.

Next, the polylactic acid-based resin microparticles will be explained in detail.

The characteristics of the porous microparticles of polylactic acid-based resin are that the number average particle diameter is small, the surface is in a porous shape, it is possible to improve lipophilic functionality and hydrophilic functionality because a considerable amount of either oil or water can be held in the pores, and because the particle diameter is small, it is possible to impart smoothness which cannot be achieved by traditional porous microparticles. Such porous microparticles of polylactic acid-based resin are suitably used in the fields such as cosmetics where achieving high performance is demanded in both oil absorption and smoothness.

With reference to the number average particle diameter of the porous microparticles of polylactic acid-based resin, it is possible to determine an appropriate range of number average particle diameter. For example, in the uses such as cosmetics, because a smaller number average particle diameter improves smoothness, the upper limit of the number average particle diameter is generally 90 µm or less, preferably 50 µm or less, more preferably 30 µm or less. Further, in the uses such as cosmetics, because coagulation of particles tends to occur when the number average particle diameter is too small, the lower limit of the number average particle diameter is generally 1 μm or more, preferably more than 1 μm, more preferably 2 μm or more, most preferably 3 μm or more.

With reference to the particle diameter distribution index showing the particle diameter distribution of the polylactic acid-based resin microparticles having porous shapes, it is preferably 2 or less because it becomes possible in the uses such as cosmetics to improve a flow of particles and impart a smoother touch. The upper limit of the particle diameter distribution index is preferably 1.5 or less, more preferably 1.3 or less, most preferably 1.2 or less. Further, the lower limit is 1 in theory.

The above-described number average particle diameter of polylactic acid-based resin microparticles having porous shapes can be calculated by measuring diameters of 100 random particles in a scanning electron microscope image and computing the arithmetic average thereof. If a shape of a particle in the SEM image is not a perfect circle, for example, an ellipse, the maximum diameter of the particle is used as its diameter. To measure the particle diameter precisely, the measurement is carried out with a magnification of at least 1000 times or more, preferably with a magnification of 5000 times or more.

Further, the particle diameter distribution index is calculated on the basis of the conversion equations described below, using measurements of the particle diameters obtained by measurement described above:

$$Dn = \sum_{i=1}^{n} Ri/n \quad \text{Equation 1}$$

$$Dv = \sum_{i=1}^{n} Ri^4 / \sum_{i=1}^{n} Ri^3$$

$$PDI = Dv/Dn$$

wherein Ri: particle diameter of single particle, n: the number of measurements (=100), Dn: number average particle diameter, Dv: volume average particle diameter, PDI: particle diameter distribution index.

Although the actual amount of pores in a porous microparticle of polylactic acid-based resin is difficult to measure directly, it is possible to use linseed oil absorption capacity as an indirect index, which is defined in pigment test methods such as Japan Industrial Standards (Refined Linseed Oil Method, JIS K 5101).

In particular, in the uses such as cosmetics and paints, higher linseed oil capability is preferable, and the lower limit of linseed oil capability is preferably 90 ml/100 g or more, more preferably 100 ml/100 g or more, further more preferably 120 ml/100 g or more, particularly preferably 150 ml/100 g or more, remarkably preferably 200 ml/100 g or more, most preferably 300 ml/100 g or more. The upper limit of linseed oil absorption capability is preferably 1000 ml/100 g or less.

Further, it is preferred that the above-described porous microparticles of polylactic acid-based resin have enthalpy of fusion of 5 J/g or more. Higher enthalpy of fusion brings higher crystallization tendency and, as a result, heat resistance and durability tend to become high. The lower limit of enthalpy of fusion is preferably 10 J/g or more, more preferably 20 J/g or more, further more preferably 30 J/g or more. Further, the upper limit is preferably 100 J/g or less. Enthalpy of fusion can be calculated from an area of peak showing thermal capacity of fusion at approximately 160 degrees Celsius in Differential Scanning calorimetry (DSC) in which a temperature is raised to 200 degrees Celsius with a temperature rise of 20 degrees Celsius per minute.

Sphericity of the above-described porous microparticles of polylactic acid-based resin is preferably 80 or more, more preferably 85 or more, further more preferably 90 or more, particularly preferably 92 or more, most preferably 95 or more. Further, in theory, the upper limit is 100. When sphericity is within the above-described range, it becomes possible to achieve an improvement in quality such as slidability. The sphericity is calculated by observing particles by a scanning electron microscope, measuring both the longest diameters and the shortest diameters of 30 random particles and subsequently substituting the measurements into the equation described below:

$$S = \frac{\sum_{i=1}^{n}(D_S/D_L)}{n} \times 100 \quad \text{Equation 2}$$

wherein S: Sphericity, n: the number of measurements (=30), $D_S$: the shortest diameter of single particle, $D_L$: the longest diameter of single particle.

On the other hand, the characteristics of the polylactic acid-based resin microparticles having smooth surfaces are that surfaces are smooth, particles are highly spherical in shape and particle diameter distribution is narrow. By using such microparticles of polylactic acid-based resin as powders, it becomes possible to improve fluidity, achieve improvements in quality such as smoothness, and increase ease of viscosity control in the case of being added to paints and the like. In addition, because such polylactic acid-based resin microparticles having smooth surfaces can move on a surface of a base member smoothly and can be fused into place on the base member homogeneously due to narrow particle diameter distribution, those particles are particularly suitable for use in the fields such as toners where excellent fluidity and low-temperature fusion characteristics are demanded.

Preferably, sphericity of the polylactic acid-based resin microparticles having smooth surfaces is 90 or more. From the viewpoint of improving mobility in the use as toners, the lower limit of sphericity is preferably 92 or more, most preferably 95 or more. Further, the upper limit is 100 in theory. Sphericity is calculated by observing particles by a scanning electron microscope, measuring both the longest diameters and the shortest diameters of 30 random particles and subsequently substituting the measurements into the equation described below:

$$S = \frac{\sum_{i=1}^{n}(D_S/D_L)}{n} \times 100 \quad \text{Equation 3}$$

wherein S means Sphericity, n means the number of measurements (=30), $D_S$ means the shortest diameter of single particle, and $D_L$ means the longest diameter of single particle.

With reference to number average particle diameter of the polylactic acid-based resin microparticles having smooth surfaces, a range of number average particle diameter can be determined appropriately in accordance with the uses. The upper limit of number average particle diameter is generally 100 μm or less, preferably 50 μm or less, more preferably 30

μm or less. Further, in the uses such as toner, because coagulation of particles tends to occur when number average particle diameter is too small, the lower limit of number average particle diameter is generally 1 μm or more, preferably more than 1 μm, more preferably 2 μm or more, most preferably 3 μm or more.

Particle diameter distribution index showing particle diameter distribution of the polylactic acid-based resin microparticles having smooth surfaces is preferably 2 or less. Because smaller particle diameter distribution index makes it possible for toners to be fused onto a substrate more homogeneously, the upper limit of particle diameter distribution index is preferably 1.8 or less, more preferably 1.5 or less, further more preferably 1.3 or less, most preferably 1.2 or less. In addition, the lower limit is 1 in theory.

The above-described number average particle diameter of polylactic acid-based resin microparticles having smooth surfaces can be calculated by measuring diameters of 100 random particles in a scanning electron microscope image and computing the arithmetic average thereof. If a shape of a particle in the SEM image is not a perfect circle, for example, an ellipse, the maximum diameter of the particle is used as its diameter. To measure the particle diameter precisely, the measurement is carried out with a magnification of at least 1000 times or more, preferably with a magnification of 5000 times or more.

Further, particle diameter distribution index is calculated on the basis of the conversion equations described below, using measurements of the particle diameters obtained by measurement described above:

$$Dn = \sum_{i=1}^{n} Ri/n \quad \text{Equation 4}$$

$$Dv = \sum_{i=1}^{n} Ri^4 / \sum_{i=1}^{n} Ri^3$$

$$PDI = Dv/Dn$$

wherein Ri: particle diameter of single particle, n: the number of measurements (=100), Dn: number average particle diameter, Dv: volume average particle diameter, PDI: particle diameter distribution index.

Although enthalpy of fusion of polylactic acid-based resin microparticles having smooth surfaces is not particularly limited, it is preferred that enthalpy of fusion is less than 5 J/g because the melting point decreases and consequently it becomes possible to use such microparticles suitably in the uses such as toners in which low-temperature fusion characteristics are demanded. The upper limit of enthalpy of fusion is preferably less than 3 J/g, more preferably less than 2 J/g, most preferably less than 1 J/g. In addition, the theoretical lower limit is 0, which indicates that polylactic acid-based resin is completely amorphous. Enthalpy of fusion can be calculated from the area of a peak showing thermal capacity of fusion at approximately 160 degrees Celsius in Differential Scanning calorimetry (DSC) in which a temperature is raised to 200 degrees Celsius with a temperature rise of 20 degrees Celsius per minute.

Furthermore, for the amount of pores in a porous microparticle of polylactic acid-based resin, linseed oil absorption capacity, which is defined in pigment test methods such as Japan Industrial Standards (Refined Linseed Oil Method, JIS K 5101), is used as an indicator.

In particular, when the above-described polylactic acid-based resin microparticles having smooth surfaces are used as toners and the like, lower linseed oil absorption capability is preferred because fusion onto a substrate takes place more homogeneously. The upper limit of linseed oil absorption capability is preferably less than 70 ml/100 g, more preferably less than 65 ml/100 g, further more preferably less than 60 ml/100 g. Further, the lower limit is preferably 30 ml/100 g.

Thus, the porous polylactic acid-based resin microparticles, which have small particle diameters and high linseed oil absorption capability, and the smooth surface polylactic acid-based resin microparticles, which have spherical shapes and narrow particle diameter distribution, are quite useful and practical for various uses in industry. Specifically, those can be used as, for example, skin care agents such as face wash, sunscreens, cleansing agents, cosmetic water, lotions, cosmetic liquid, creams, cold creams, aftershave lotions, shaving soaps, oil absorbing sheets and matifiants, cosmetics and modification agents thereof such as foundations, foundation powder, face powder in liquid form, mascara, face powder, Dohran, eyebrow pencil, mascara, eye line, eye shadow, eye shadow base, nose shadow, lipsticks, gloss, cheek brushes, tooth wax, manicure and topcoat, additives for hair care products such as shampoo, dry shampoo, conditioner, rinse, shampoo containing rinse ingredients, treatment, hair tonic, hair conditioner, hair oil, pomade and hair color agent, additives for amenity products such as perfume, cologne, deodorant, baby powder, tooth powder, mouthwash, lip balm and soap, rheology improving agents such as an additive for toner and paint, diagnostic test agents for medical purpose, machine characteristics improving agents for molded products such as car materials and building materials, machine characteristics improving materials such as film and fiber, raw materials for molding resin such as rapid prototyping and rapid manufacturing, flash-moldable material, paste resin for plastic sol, powder blocking agent, various modifying agents such as powder flowability improving agent, lubricant, rubber compounding ingredient, polishing agent, viscosity improver, filter material/filter aid, gelatinizer, coagulation agent, additive for paints, oil absorbing material, mold releasing agent, slippage improving agent for plastic films/sheets, antiblocking agent, gloss adjusting agent, frosted finish agent, light diffusion agent, surface hardness improving agent and ductility improving material, spacer for liquid crystal display equipment, filler/carrier for chromatography, base material/additive for cosmetic foundation, assistant for micro-capsules, medical materials for drug delivery system/diagnostic reagents, support agent for perfume/pesticide, catalyst/carrier for chemical reactions, gas adsorption agent, sintered material for ceramic processing, standard particle material for measurement/analysis, particle material for food manufacture industry, material for powder coating, and toner for electrophotographic development.

Furthermore, polylactic acid-based resin microparticles have the potential to substitute traditionally used polymer microparticles because they are materials of non-petroleum origin and have characteristics as low environmental load materials. Electricity, the electronic parts which are represented, for example, for concrete uses such as the resin molding body mentioned above, a film, the fiber by the housing of the electric apparatus, the housing of the OA apparatus, various covers, various gears, various cases, a sensor, an LED lamp, a connector, a socket, a resistor, a relay case, a switch, various terminal boards, a plug, a printed wiring board, a tuner, a speaker, a microphone, headphones, a small size motor, a magnetic head base, a power module, a housing, a semiconductor, liquid crystal, FDD carriage, FDD chassis, a motor brush holder, a parabolic antenna, a computer connection part. The applications of the above-described such as resin moldings, films and fibers include, for example, electric or electronic parts, typified by a housing of an electric apparatus, a housing of an OA apparatus, various covers, various gears, various cases, a sensor, an LED lamp, a connector, a socket, a resistor, a relay case, a switch, various terminal boards, a plug, a printed wiring board, a tuner, a speaker, a microphone, headphones, a small size motor, a magnetic head base, a power module, a housing, a semiconductor, liquid crystal, FDD carriage, FDD chassis, a motor brush holder, a parabolic antenna and a computer connection part, TV parts, irons, hair dryers, rice cooker parts, microwave oven parts, audio equipment parts such as a sound part, an audio, a laser disc (a registered trademark) and a compact disk, video equipment-related parts such as a camera, a VCR, a picture-taking lens (for projection TV, etc.), a finder, a filter, a prism and Fresnel lens, home and office electric appliance parts such as an illumination part, a refrigerator part, an air-conditioner part, a typewriter part and a word processor part, information appliance-related parts such as an office computer-related part, a telephone-related part, a facsimile-related part, a copier-related part, films for protecting various disk boards, a Laser Disk player pickup lens, optical fiber, a light switch and an optical connector, liquid crystal display, flat-panel display, light guiding panel for plasma display, Fresnel lens, polarizing plate, polarizing plate protection film, phase difference film, light diffusion film, angle of field expansion film, reflection film, reflection prevention film, anti-glare film, brightness improvement film, prism sheet and light guiding film for touch panel, machine-related parts, typified by a jig for washing, a motor part, a writer and a typewriter, Optical equipments typified by a microscope, binoculars and a clock, precision instrument-related parts, various pipes for fuel, exhaustion and intake, an air intake nozzle snorkel, intake manifold, a fuel pump, a connector for fuses, Horne terminal, an electric equipment part insulation board, a lamp socket, a lamp reflector, a lamp housing, an engine oil filter and an ignition case, and are remarkably useful for such various uses.

EXAMPLES

Hereinafter, our processes, microparticles and cosmetics will be explained in detail based on examples, but this disclosure is not limited to these examples.

(1) Measuring Methods for Enthalpy of Fusion and Crystallization Temperature:

Enthalpy of fusion was calculated from area size of a peak, which appears at approximately 160 degrees Celsius and shows thermal capacity of fusion, in carrying out a measurement up to 200 degrees Celsius with a temperature rise of 20 degrees Celsius per minute by using a differential scanning calorimeter (robot DSC RDC220, supplied by SEIKO Instruments Inc.) under nitrogen atmosphere.

Further, the crystallization temperature was determined as a vertex temperature of a crystallization temperature peak, which appears in a range approximately from 80 to 130 degrees Celsius during cooling, in carrying out a measurement with a temperature drop of 1 degree Celsius per minute after having raised the temperature up to 200 degrees Celsius by using the above-described instrument under the same conditions.

(2) Weight Average Molecular Mass:
(i) Determination of Molecular Weight of the Polylactic Acid-Based Resin (A):

The weight average molecular mass was calculated by using gel permeation chromatography with reference to the calibration curve of polymethyl methacrylate (PMMA).
    Device: LC system supplied by Waters Corporation
    Columns: two HFIP-806Ms supplied by Showa Denko K.K.
    Mobile phase: sodium trifluoroacetate 10 mmol/L hexafluoroisopropanol solution
    Flow rate: 1.0 ml/min
    Detector: refractive index detector
    Column temperature: 30 degrees Celsius (ii) Determination of Molecular Weight of the Polymer (B) Different from Polylactic Acid-Based Resin:

The weight average molecular mass was calculated by using gel permeation chromatography with reference to the calibration curve of polymethyl methacrylate (PMMA).
    Device: LC-10A series supplied by Shimazu Corporation
    Columns: two GF-7 MHQs supplied by Showa Denko K.K.
    Mobile phase: 10 mmol/L lithium bromide water solution
    Flow rate: 1.0 ml/min
    Detector: refractive index detector
    Column temperature: 40 degrees Celsius (3) Determination of Interfacial Tension In reference to a solution phase of polylactic acid-based resin (A) and a solution phase of polymer (B) different from polylactic acid-based resin, liquid-air surface tensions, r1 and r2 respectively, of both phases were measured on a hot plate by using an automatic contact angle meter DM-501 supplied by Kyowa Interface Science Co., Ltd., and interfacial tension was calculated from the absolute value of the differential (r1−r2).

(4) Measuring Methods for Average Particle Diameter and Particle Diameter Distribution:

Each particle diameter of microparticles was measured by a scanning electron microscope (JSM-6301NF, a scanning electron microscope supplied by JEOL Ltd.) with a magnification of 1,000 times. When a particle was not spherical, the longest diameter was measured as the particle diameter thereof.

Average particle diameter was calculated by measuring particle diameters of 100 random particles in a scanning electron microscope image and computing the arithmetic average thereof.

Particle diameter distribution index showing distribution of particle diameters was calculated on the basis of the following conversion equations, using measurement values of particle diameters obtained by the above-described measurement:

$$Dn = \sum_{i=1}^{n} Ri/n$$

$$Dv = \sum_{i=1}^{n} Ri^4 \bigg/ \sum_{i=1}^{n} Ri^3$$

$$PDI = Dv/Dn.$$

Equation 5

In the equations above, Ri means particle diameter of single particle, n means the number of measurements (=100), Dn means number average particle diameter, Dv means volume average particle diameter, and PDI means particle diameter distribution index.

(5) Determination of Sphericity:

Sphericity was calculated by observing particles with a scanning electron microscope, measuring both the longest and shortest diameters of each of 30 random particles, and assigning the measurement values to the following equation:

$$S = \frac{\sum_{i=1}^{n}(D_S/D_L)}{n} \times 100. \qquad \text{Equation 6}$$

In the equations above, S means Sphericity, n means the number of measurements (=30), $D_S$ means the shortest diameter of a single particle, and $D_L$ means the longest diameter of a single particle.

(6) Determination of Linseed Oil Absorption Capacity:

For an evaluation of the oil absorption capacity which is an index of porosity of polylactic acid-based resin microparticles, Japan Industrial Standards (JIS) K 5101 "Pigment Test Method Refined Linseed Oil Method" was used. Approximately 100 mg of polylactic acid-based resin microparticles were weighed on a watch glass with high precision. Then, refined linseed oil (supplied by Kanto Chemical Co., Inc.) was added thereto drop by drop with a burette and was kneaded by a palette knife. The adding-kneading process was repeated until the sample turns into a lump, and the endpoint was determined as a point where the sample paste exhibited smooth hardness. Oil absorption capacity (ml/100 g) was calculated from the amount of refined linseed oil used in the process.

Production Example 1

Process 1 for Producing Polylactic Acid 70.2 g of L-lactide (supplied by Sigma-Aldrich Co. LLC.: more than 98% ee in optical purity), 30.1 g of D-lactide (supplied by Sigma-Aldrich Co. LLC.: more than 98% ee in optical purity) and 1.1 g of octanol were put in a reaction tank having a mixing machine and were dissolved homogeneously at a temperature of 150 degrees Celsius under nitrogen atmosphere. Then, 0.90 g of tin octylate (supplied by Sigma-Aldrich Co. LLC.) was added thereto as a toluene solution in which concentration ratio was adjusted to 10 mass % of dry toluene, and polymerization reaction was performed for six hours. After the polymerization reaction had finished, reactant was dissolved in chloroform and reprecipitated in methanol with being stirred, and a solid matter was obtained by removing monomers and catalysts therefrom. By performing filtration of the solid matter obtained and performing vacuum heat-drying at 80 degrees Celsius, polylactic acid-based resin having an copolymerization ratio L/D of 70/30, an enthalpy of fusion of 0 J/g and Mw of 11200 (in terms of PMMA) was obtained. The SP value of this polymer was 23.14 $(J/cm^3)^{1/2}$ according to the above-described computational method.

Production Example 2

Process 2 for Producing Polylactic Acid

A polylactic acid-based resin was produced in a manner similar to Production Example 1 except that 49.9 g of L-lactide (supplied by Sigma-Aldrich Co. LLC.: more than 98% ee in optical purity), 49.8 g of D-lactide (supplied by Sigma-Aldrich Co. LLC.: more than 98% ee in optical purity) and 0.95 g of tin octylate (supplied by Sigma-Aldrich Co. LLC.) were used. The polylactic acid-based resin obtained had a copolymerization ratio L/D of 50/50, an enthalpy of fusion of 0 J/g and Mw (in terms of PMMA) of 9,800. The SP value of this polymer was 23.14 $(J/cm^3)^{1/2}$ according to the above-described computational method.

Production Example 3

Process 3 for Producing Polylactic Acid

A polylactic acid-based resin was produced in a manner similar to Production Example 1 except that 70.1 g of L-lactide (supplied by Sigma-Aldrich Co. LLC.: more than 98% ee in optical purity), 29.8 g of D-lactide (supplied by Sigma-Aldrich Co. LLC.: more than 98% ee in optical purity) and 0.90 g of tin octylate (supplied by Sigma-Aldrich Co. LLC.) were used. The polylactic acid-based resin obtained had a copolymerization ratio L/D of 70/30, an enthalpy of fusion of 0 J/g and Mw (in terms of PMMA) of 98,000. The SP value of this polymer was 23.14 $(J/cm^3)^{1/2}$ according to the above-described computational method.

Example 1

0.5 g of polylactic acid (L/D=98.8/1.2, Mw (in terms of PMMA)=160,000, enthalpy of fusion=31.1 J/g, SP value=23.14 $(J/cm^3)^{1/2}$), 0.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 9.0 g of tetrahydrofuran as an ether-based organic solvent were put in a 100 ml four-neck flask, heated to 50 degrees Celsius, and stirred until the polymers have been dissolved completely. After bringing the temperature back to room temperature, 5 g of ion exchanged water as a poor solvent was added by dripping it with a pipette while stirring with a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 0.4 g of white solid was obtained in powder form. According to an observation with a scanning electron microscope, the powder obtained was polylactic acid microparticles having a porous microparticle shape, having an average particle diameter of 33.0 μm and a particle diameter distribution index of 1.55.

Example 2

1.5 g of polylactic acid (L/D=98.8/1.2, Mw (in terms of PMMA)=160,000, enthalpy of fusion=31.1 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 46.0 g of tetrahydrofuran as an ether-based organic solvent were put in a 100 ml four-neck flask, heated to 50 degrees Celsius, and stirred until the polymers have been dissolved completely. After bringing the temperature back to room temperature, 50 g of ion exchanged water as a poor solvent was added by dripping it with a pump at a speed of 0.41 g per minute while stirring with a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 0.4 g of white solid was obtained in powder form. According to an observation with a scanning electron microscope, the powder obtained was polylactic acid microparticles having a porous microparticle shape, having an average particle diameter of 25.1 μm, having a particle diameter distribution index of 1.35, having a sphericity of 89 and linseed oil absorption of 432 ml/100 g. Further, the enthalpy of fusion of these polylactic acid microparticles was 57.8 J/g. An observation diagram of these microparticles by a scanning electron microscope is shown in FIG. 1.

Example 3

2.5 g of polylactic acid (L/D=98.8/1.2, Mw (in terms of PMMA)=160,000, enthalpy of fusion=31.1 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 45.0 g of tetrahydrofuran as an ether-based organic solvent were put in a 100 ml four-neck flask, heated to 50 degrees Celsius, and stirred until the polymers were completely dissolved. After bringing the temperature back to room temperature, 50 g of ion exchanged water as a poor solvent was added by dripping it with a pump at a speed of 0.41 g per minute while stirring with a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 2.2 g of white solid was obtained in powder form. According to an observation with a scanning electron microscope, the powder obtained was polylactic acid microparticles having a porous microparticle shape, having an average particle diameter of 59.5 μm, having a particle diameter distribution index of 11.5 and a linseed oil absorption of 661 ml/100 g.

Example 4

Figure 2:
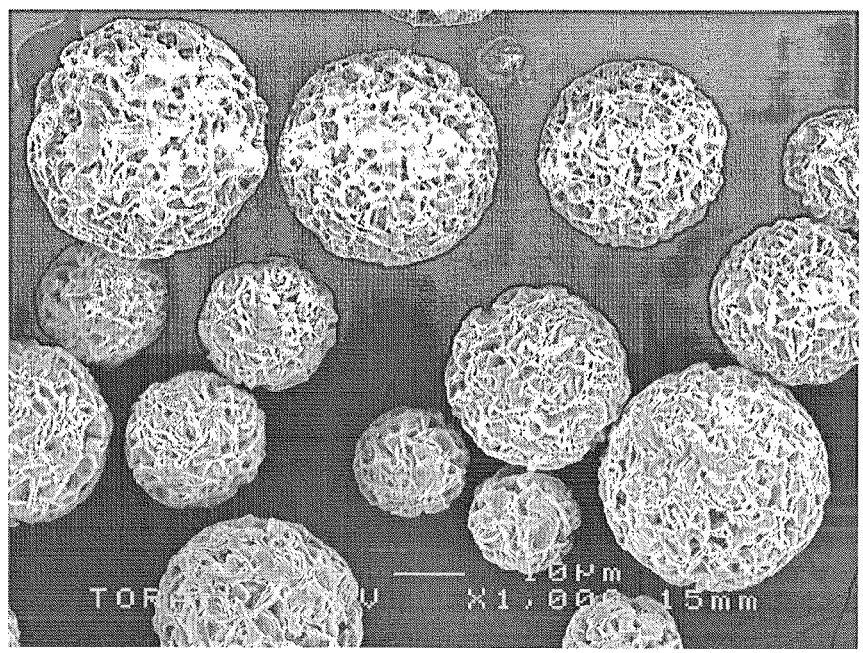
FIG. 2 is an observation diagram by a scanning electron microscope, showing polylactic acid-based resin microparticles produced in Practical Example 4.

2.5 g of polylactic acid (L/D=98.8/1.2, Mw (in terms of PMMA)=160,000, enthalpy of fusion=31.1 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid, 33.75 g of diethylene glycol dimethyl ether (diglyme) as an ether-based organic solvent and 11.25 g of N-methyl-2-pyrrolidone as an other organic solvent were put in a 100 ml four-neck flask, heated to 80 degrees Celsius, and stirred until the polymers have been dissolved completely. With the temperature maintained, 50 g of ion exchanged water as a poor solvent was added by dripping it with a pump at a speed of 0.82 g per minute while stirring with a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 2.4 g of white solid was obtained in powder form. According to an observation with a scanning electron microscope, the powder obtained was polylactic acid microparticles having a porous microparticle shape, having an average particle diameter of 13.7 μm, having a particle diameter distribution index of 1.24, having a sphericity of 82 and a linseed oil absorption of 524 ml/100 g. Further, the enthalpy of fusion of these polylactic acid microparticles was 58.2 J/g. An observation diagram of these microparticles by a scanning electron microscope is shown in FIG. 2.

Example 5

Figure 3:
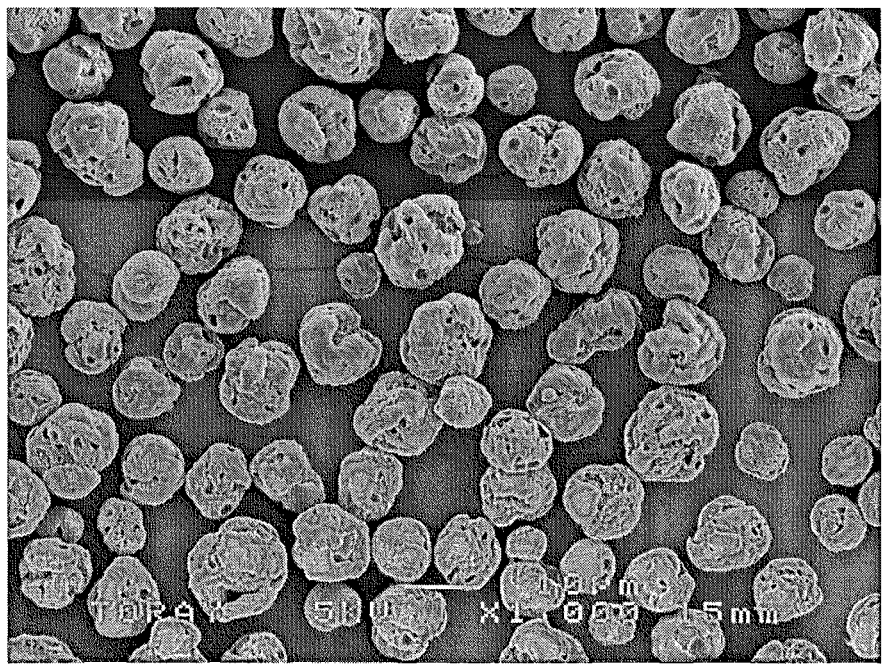
FIG. 3 is an observation diagram by a scanning electron microscope, showing polylactic acid-based resin microparticles produced in Practical Example 5.

1.5 g of polylactic acid (L/D=96/4, Mw (in terms of PMMA)=150,000, enthalpy of fusion=28.6 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 46.0 g of tetrahydrofuran as an ether-based organic solvent were put in a 100 ml four-neck flask, heated to 60 degrees Celsius, and stirred until the polymers have been dissolved completely. After bringing the temperature back to room temperature, 50 g of ion exchanged water as a poor solvent was added by dripping it with a pump at a speed of 0.41 g per minute while stirring with a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 1.3 g of white solid was obtained in powder form. According to an observation with a scanning electron microscope, the powder obtained was polylactic acid microparticles having a porous microparticle shape, having an average particle diameter of 10.0 μm, having a particle diameter distribution index of 1.10, having a sphericity of 85 and a linseed oil absorption of 96 ml/100 g. Further, the enthalpy of fusion of these polylactic acid microparticles was 34.3 J/g. An observation diagram of these microparticles by a scanning electron microscope is shown in FIG. 3.

Example 6

2.5 g of polylactic acid (L/D=96/4, Mw (in terms of PMMA)=150,000, enthalpy of fusion=28.6 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 45.0 g of diethylene glycol dimethyl ether as an ether-based organic solvent were put in a 100 ml four-neck flask, heated to 80 degrees Celsius, and stirred until the polymers had been dissolved completely. With the temperature maintained, 50 g of ion exchanged water as a poor solvent was added by dripping it with a pump at a speed of 0.82 g per minute while stirring with a stirrer. Stirring was continued for another 30 minutes after the whole amount of the water has been dropped, and the resulting suspension was filtered and washed by 50 g of ion exchanged water. Then, by drying the filtered matter in vacuum at 80 degrees Celsius for 10 hours, 2.3 g of white solid was obtained in powder form. According to an observation with a scanning electron microscope, the powder obtained was a polylactic acid microparticle having a porous microparticle shape, having an average particle diameter of 14.0 μm, having a particle diameter distribution index of 1.25, having a sphericity of 93 and a linseed oil absorption of 149 ml/100 g. Further, the enthalpy of fusion of these polylactic acid microparticles was 32.6 J/g.

Example 7

Figure 4:
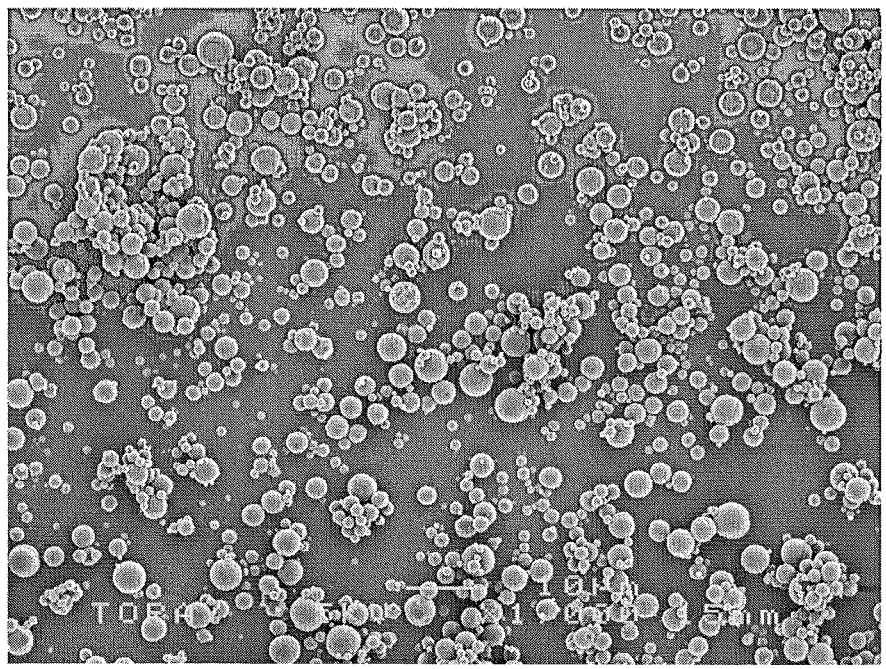
FIG. 4 is an observation diagram by a scanning electron microscope, showing polylactic acid-based resin microparticles produced in Practical Example 7.

1.5 g of polylactic acid (L/D=98.8/1.2, Mw (in terms of PMMA)=160,000, enthalpy of fusion=31.1 J/g, SP value=23.14 $(J/cm^3)^{1/2}$, crystallization temperature during cooling=108 degrees Celsius), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 46.0 g of diethylene glycol dimethyl ether as an ether-based organic solvent were put in a 100 ml autoclave, heated to 140 degrees Celsius, and stirred until the polymers have been dissolved completely. With the temperature maintained, 50 g of ion exchanged water as a poor solvent was added by dripping it with a pump at a speed of 0.41 g per minute while stirring with a stirrer. Stirring was continued for another 30 minutes after the whole amount of water had been added, and a suspension obtained was filtered and washed by 50 g of ion exchanged water. Then, by drying the filtered matter in vacuum at 80 degrees Celsius for 10 hours, 1.3 g of white solid was obtained in powder form. According to an observation with a scanning electron microscope, the powder obtained was polylactic acid microparticles having a smooth surface microparticle shape, having an average particle diameter of 1.6 μm, having a particle diameter distribution index of 1.40, having a sphericity of 95 and a linseed oil absorption of 51 ml/100 g. Further, the enthalpy of fusion of these polylactic acid microparticles was 40.8 J/g. An observation diagram of these microparticles by a scanning electron microscope is shown in FIG. 4.

Example 8

1.5 g of polylactic acid (L/D=96/4, Mw (in terms of PMMA)=150,000, enthalpy of fusion=28.6 J/g, SP value=23.14 $(J/cm^3)^{1/2}$, crystallization temperature during cooling=108 degrees Celsius), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 46.0 g of diethylene glycol dimethyl ether as an ether-based organic solvent were put in a 100 ml autoclave, heated to 140 degrees Celsius, and stirred until the polymers have been dissolved completely. While keeping the system temperature, 50 g of ion exchanged water as a poor solvent was added by dripping it with a pump at a speed of 0.41 g per minute while stirring a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 1.3 g of white solid was obtained in powder form. According to an observation with a scanning electron microscope, the powder obtained was polylactic acid microparticles having a smooth surface microparticle shape, having an average particle diameter of 1.8 μm, having a particle diameter distribution index of 1.82, having a sphericity of 97 and a linseed oil absorption of 58 ml/100 g. Further, an enthalpy of fusion of these polylactic acid microparticles was 30.4 J/g.

Example 9

Figure 5:
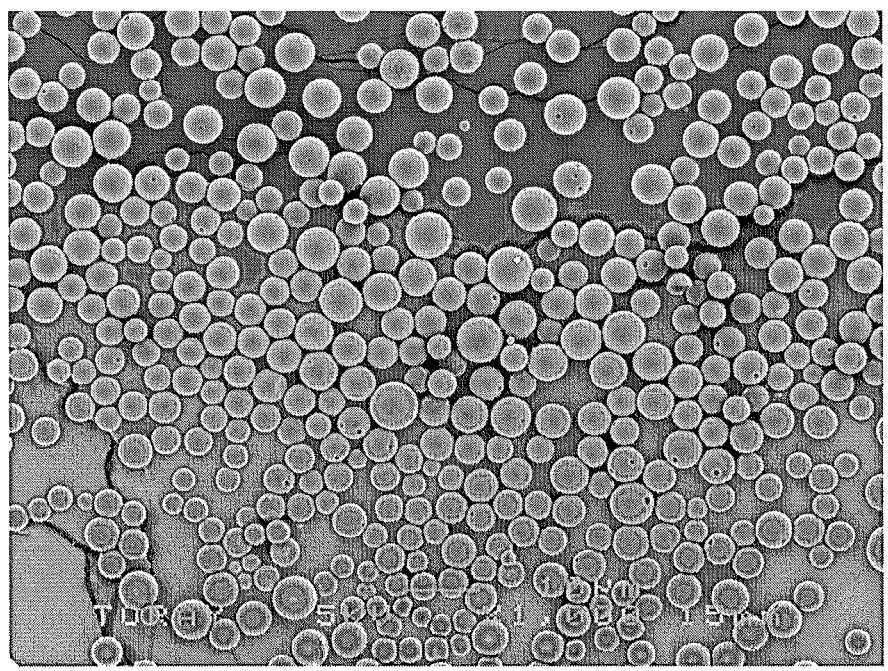
FIG. 5 is an observation diagram by a scanning electron microscope, showing polylactic acid-based resin microparticles produced in Practical Example 9.

1.5 g of polylactic acid (L/D=88/12, Mw (in terms of PMMA)=150,000, enthalpy of fusion=0 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 46.0 g of tetrahydrofuran as an ether-based organic solvent were put in a 100 ml four-neck flask, heated to 60 degrees Celsius, and stirred until the polymers have been dissolved completely. After bringing the temperature back to room temperature, 50 g of ion exchanged water as a poor solvent was added by dripping it with a pump at a speed of 0.41 g per minute while stirring a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 1.3 g of white solid was obtained in powder form. According to an observation with a scanning electron microscope, the powder obtained was polylactic acid microparticles having a smooth surface microparticle shape, having an average particle diameter of 4.5 μm, having a particle diameter distribution index of 1.1, having a sphericity of 95 and a linseed oil absorption of 58 ml/100 g. Further, an enthalpy of fusion of these polylactic acid microparticles was 0 J/g. An observation diagram of these microparticles by a scanning electron microscope is shown in FIG. 5.

Example 10

By performing a procedure as in Practical Example 9 except for using the polylactic acid of Production Example 1, 1.3 g of white solid was obtained in powder form. According to an observation with a scanning electron microscope, the powder obtained was polylactic acid microparticles having a smooth surface microparticle shape, having an average particle diameter of 7.8 μm, having a particle diameter distribution index of 1.31 and a sphericity of 91.

Example 11

By performing a procedure as in Practical Example 9 except for using the polylactic acid of Production example 2, 1.3 g of white solid was obtained in powder form. According to an observation with a scanning electron microscope, the powder obtained was polylactic acid microparticles having a smooth surface microparticle shape, having an average particle diameter of 10.2 μm, having a particle diameter distribution index of 1.20 and a sphericity of 94.

Example 12

By performing a procedure as in Practical Example 9 except for using the polylactic acid of Production example 3, 1.3 g of white solid was obtained in powder form. According to an observation with a scanning electron microscope, the powder obtained was polylactic acid microparticles having a smooth surface microparticle shape, having an average particle diameter of 12.1 μm, having a particle diameter distribution index of 1.33 and a sphericity of 90.

Example 13

2.5 g of polylactic acid (L/D=88/12, Mw (in terms of PMMA)=150,000, enthalpy of fusion=0 J/g, SP value=23.14 $(J/cm^3)^{1/2}$), 2.5 g of hydroxypropyl cellulose (supplied by Tokyo Chemical Industry Co., Ltd., weight average molecular mass=118,000, SP value=29.0 $(J/cm^3)^{1/2}$) as a polymer different from polylactic acid and 45.0 g of diethylene glycol dimethyl ether as an ether-based organic solvent were put in a 100 ml four-neck flask, heated to 80 degrees Celsius, and stirred until the polymers have been dissolved completely. With the temperature maintained, 50 g of ion exchanged water as a poor solvent was added by dripping it with a pump for an hour while stirring with a stirrer. Stirring was continued for another 30 minutes after the whole amount of water had been added, and the resulting suspension was filtered and washed by 50 g of ion exchanged water. Then, by drying the filtered matter in vacuum at 80 degrees Celsius for 10 hours, 1.3 g of white solid was obtained in powder form. According to an observation with a scanning electron microscope, the powder obtained was polylactic acid microparticles having a smooth surface microparticle shape, having an average particle diameter of 10.2 μm, having a particle diameter distribution index of 1.32, having a sphericity of 94 and a linseed oil absorption of 67 ml/100 g. Further, an enthalpy of fusion of these polylactic acid microparticles was 0 J/g.

Comparative Example 1

1.5 g of polylactic acid (L/D=98.8/1.2, Mw (in terms of PMMA)=160,000, enthalpy of fusion=31.1 J/g, the SP value=23.14 $(J/cm^3)^{1/2}$), 2.5 g of hydroxypropyl cellulose (supplied by Tokyo Chemical Industry Co., Ltd., weight average molecular mass=118,000, the SP value=29.0 $(J/cm^3)^{1/2}$) as a polymer different from polylactic acid and 46.0 g of N-methyl-2-pyrrolidone as an alternative to an ether-based organic solvent were put in a 100 ml autoclave, heated to 50 degrees Celsius, and stirred until the polymers have been dissolved completely. After bringing the temperature back to room temperature, 50 g of ion exchanged water as a poor solvent was added by dripping it with a pump at a speed of 0.41 g per minute while stirring with a stirrer. Stirring was continued for another 30 minutes after the whole amount of water had been added. When filtering the resulting slurry liquid, handling was not easy and it was difficult to extract it in powder form. According to measurements of volume average particle diameter and number average particle diameter in slurry state by using a laser diffraction particle size analyzer (supplied by Shimadzu Corporation, SALD-2100), the microparticles obtained had an average particle diameter (volume average particle diameter) of 24.3 μm and a particle diameter distribution index of 9.1.

Comparative Example 2

5 g of polylactic acid (D-isomer=1.2%, Mw (in terms of PMMA)=160,000, melting point=168 degrees Celsius) and 50.0 g of diethylene glycol dimethyl ether (diglyme) as an ether-based organic solvent were put in a 100 ml four-neck flask, and were dissolved in an oil bath under heat reflux conditions. After the temperature was cooled down slowly to room temperature by switching off the oil bath, a suspension of polylactic acid-based microparticles was obtained. The suspension was filtered and washed by 50 g of ion exchanged water, and by drying the filtered matter in vacuum at 80 degrees Celsius for 10 hours, 4.88 g of white solid was obtained in powder form. According to an observation with a scanning electron microscope, the powder obtained was polylactic acid microparticles having a porous microparticle shape, having an average particle diameter of 64.0 μm, having a particle diameter distribution index of 3 or more and a sphericity of 50 or less.

Comparative Example 3

Figure 6:
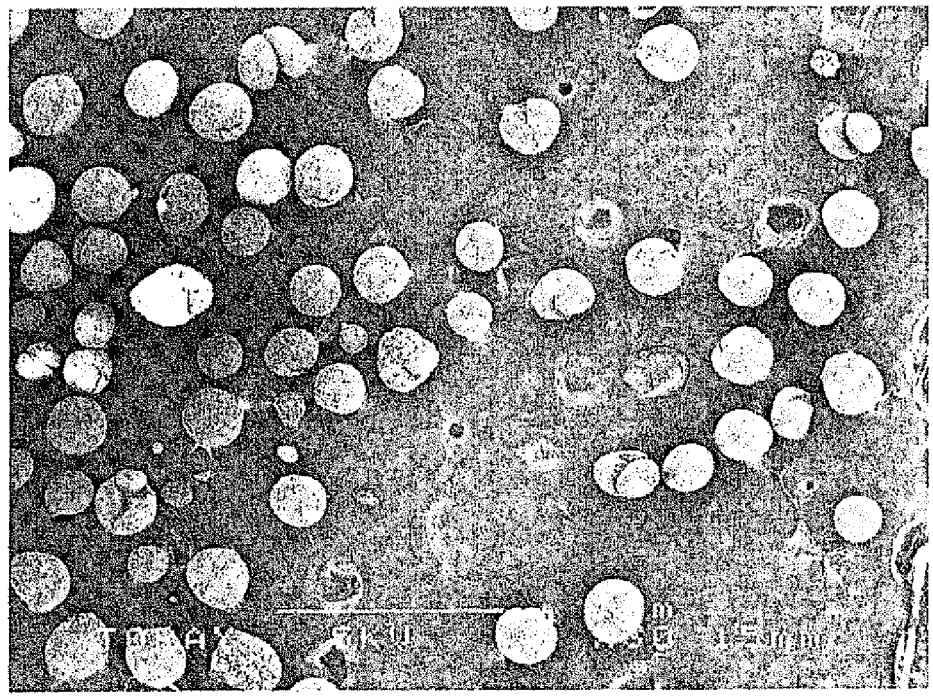
FIG. 6 is an observation diagram by a scanning electron microscope, showing polylactic acid-based resin microparticles produced in Comparative Example 3.

Polylactic acid-based resin microparticles were prepared according to a procedure disclosed in JP-A-2009-242728. 1.0 g of polylactic acid (L/D=98.8/1.2, Mw (in terms of PMMA)=160,000, enthalpy of fusion=31.1 J/g, SP value=23.14 $(J/cm^3)^{1/2}$) and 9.0 g of orthodichlorobenzene were put in a 100 ml autoclave, heated to 160 degrees Celsius and dissolved completely. The autoclave was immersed in an oil bath of 30 degrees Celsius for 15 minutes, and the resulting powder was filtered and washed by 50 g of ion exchanged water. By drying the filtered matter in vacuum at 80 degrees Celsius for 10 hours, 0.9 g of white solid was obtained in powder form. According to an observation with a scanning electron microscope, the powder obtained was polylactic acid microparticles having a porous microparticle shape, having an average particle diameter of 234.3 μm, having a particle diameter distribution index of 1.10, having a sphericity of 86 and a linseed oil absorption of 86 ml/100 g. Further, the enthalpy of fusion of these polylactic acid microparticles was 21.2 J/g. An observation diagram of these microparticles by the scanning electron microscope is shown in FIG. 6.

Comparative Example 4

Figure 7:
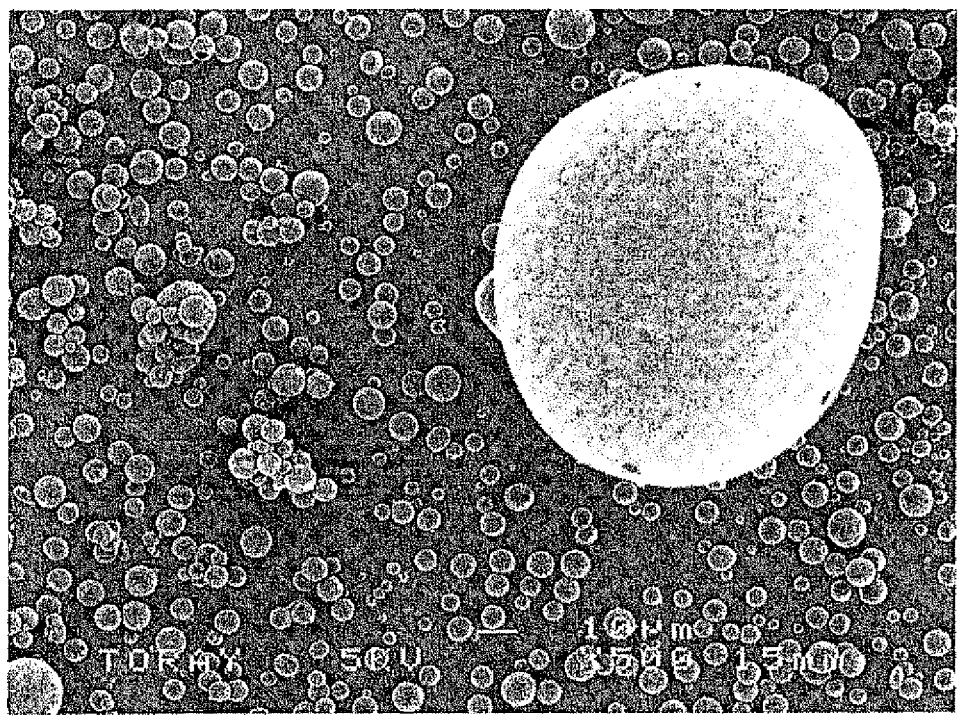
FIG. 7 is an observation diagram by a scanning electron microscope, showing polylactic acid-based resin microparticles produced in Comparative Example 4.

Polylactic acid-based resin microparticles were prepared according to a procedure disclosed in JP-A-2004-269865. 24.0 g of polylactic acid (L/D=98.8/1.2, Mw (in terms of PMMA)=160,000, enthalpy of fusion=31.1 J/g, SP value=23.14 $(J/cm^3)^{1/2}$), 40.0 g of oligosaccharide (hydrogenated starch hydrolysate PO-10 supplied by Mitsubishi Shoji Foodtech Co., Ltd.) and 16.0 g of pentaerythritol were put in a Labo-Plast Mill at a temperature of 200 degrees Celsius, and were kneaded for 5 minutes at a speed of 50 rotations per minute. After cooling, a resulting lump matter was added to ion exchanged water, washed at a temperature of 60 degrees Celsius and filtered. By drying the filtered matter in vacuum at 80 degrees Celsius for 10 hours, 21.0 g of white solid was obtained in powder form. According to an observation with a scanning electron microscope, the powder obtained was polylactic acid microparticles having a smooth surface microparticle shape, having an average particle diameter of 6.1 μm, having a particle diameter distribution index of 17.1, having a sphericity of 94 and a linseed oil absorption of 56 ml/100 g. Further, the enthalpy of fusion of these polylactic acid microparticles was 38.8 J/g. An observation diagram of these microparticles by the scanning electron microscope is shown in FIG. 7.

Comparative Example 5

Figure 8:
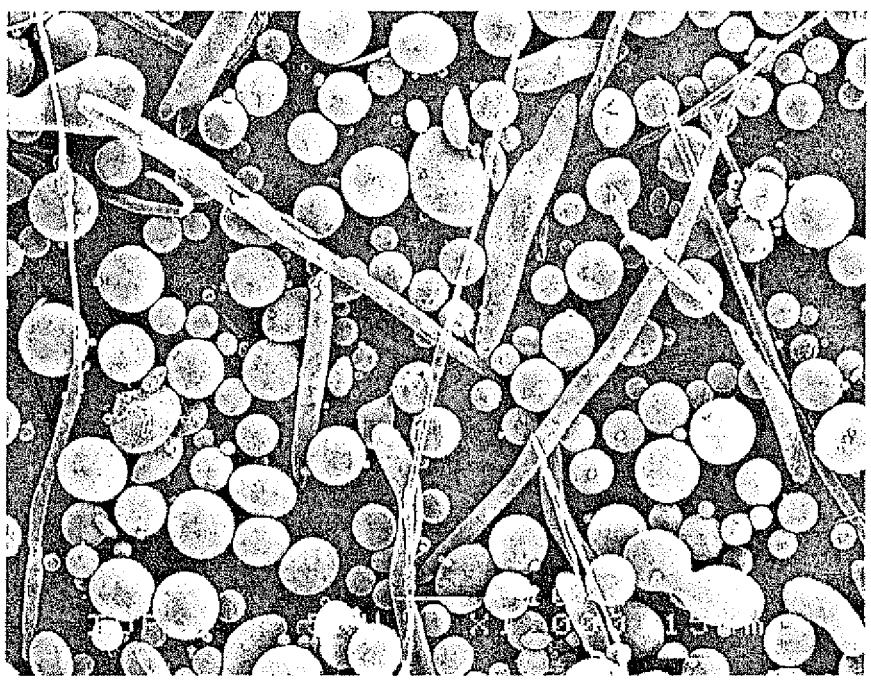
FIG. 8 is an observation diagram by a scanning electron microscope, showing polylactic acid-based resin microparticles produced in Comparative Example 5.

Polylactic acid-based resin microparticles were prepared according to a procedure disclosed in JP-A-2004-269865. 24.0 g of polylactic acid (L/D=88/12, Mw (in terms of PMMA)=150,000, enthalpy of fusion=0 J/g, SP value=23.14 $(J/cm^3)^{1/2}$), 40.0 g of oligosaccharide (hydrogenated starch hydrolysate PO-10 supplied by Mitsubishi Shoji Foodtech Co., Ltd.) and 16.0 g of pentaerythritol were put in a Labo-Plast Mill at a temperature of 200 degrees Celsius, and were kneaded for 5 minutes at a speed of 50 rotations per minute. After cooling, a resulting lump matter was added to ion exchanged water, washed at a temperature of 60 degrees Celsius and filtered. By drying the filtered matter in vacuum at 80 degrees Celsius for 10 hours, 21.5 g of white solid was obtained in powder form. According to an observation with a scanning electron microscope, the powder obtained was polylactic acid microparticles including smooth surface microparticles and fiber-shaped ones, having an average particle diameter of 4.7 μm, having a particle diameter distribution index of 6.2, having a sphericity of 79 and a linseed oil absorption of 54 ml/100 g. Further, the enthalpy of fusion of these polylactic acid microparticles was 0 J/g. An observation diagram of these microparticles by the scanning electron microscope is shown in FIG. 8.

Comparative Example 6

Polylactic acid-based resin microparticles were prepared according to a procedure disclosed in JP-A-2005-002302. 1.4 g of polylactic acid (L/D=98.8/1.2, Mw (in terms of PMMA) 160,000, enthalpy of fusion=31.1 J/g, SP value 23.14 $(J/cm^3)^{1/2}$) was dissolved completely in 12.6 g of 1,3-dioxolane, and subsequently 7.0 g of ethyl acetate was added thereto. 21.0 g of water was dropped for 20 minutes while being stirred by a homogenizer, however, it was not possible to obtain microparticles because a lump matter was formed instead.

Comparative Example 7

Polylactic acid-based resin microparticles were prepared according to a procedure disclosed in JP-A-2005-002302. 1.4 g of polylactic acid (L/D=88/12, Mw (in terms of PMMA) 150,000, enthalpy of fusion=0 J/g, SP value 23.14 $(J/cm^3)^{1/2}$) was dissolved completely in 12.6 g of 1,3-dioxolane, and subsequently 7.0 g of ethyl acetate was added thereto. 21.0 g of water was dropped for 20 minutes while being stirred by a homogenizer, however, it was not possible to obtain microparticles because a lump matter was formed instead.

As for Examples 1-13 and Comparative Examples 1-7, the conditions of production processes are shown in Table 1, and the measurement results regarding the polylactic acid-based resin microparticles obtained are shown in Table 2.

TABLE 1

| | Polylactic Acid-based Resin (A) | Polymer (B) different from polylactic acid-based resin | Organic Solvent (C) | | | | Poor Solvent |
|---|---|---|---|---|---|---|---|
| | | | Ether-based | | | | |
| | Enthalpy of Fusion (J/g) | Type | Type | Boiling Point (° C.) | Other Organic Solvent | Mass Ratio (Ether-based/Others) | Contact Temperature (° C.) |
| Example 1 | 31.1 | hydroxypropyl cellulose | tetrahydrofuran | 60 | — | — | 30 |
| Example 2 | 31.1 | hydroxypropyl cellulose | tetrahydrofuran | 60 | — | — | 30 |
| Example 3 | 31.1 | hydroxypropyl cellulose | tetrahydrofuran | 60 | — | — | 30 |
| Example 4 | 31.1 | hydroxypropyl cellulose | diglyme | 160 | N-methyl-2-pyrrolidone | 75/25 | 80 |
| Example 5 | 28.6 | hydroxypropyl cellulose | tetrahydrofuran | 60 | — | — | 30 |
| Example 6 | 28.6 | hydroxypropyl cellulose | diglyme | 160 | — | — | 80 |
| Example 7 | 31.1 | hydroxypropyl cellulose | diglyme | 160 | — | — | 140 |
| Example 8 | 28.6 | hydroxypropyl cellulose | diglyme | 160 | — | — | 140 |
| Example 9 | 0 | hydroxypropyl cellulose | tetrahydrofuran | 60 | — | — | 30 |
| Example 10 | 0 | hydroxypropyl cellulose | tetrahydrofuran | 60 | — | — | 30 |
| Example 11 | 0 | hydroxypropyl cellulose | tetrahydrofuran | 60 | — | — | 30 |
| Example 12 | 0 | hydroxypropyl cellulose | tetrahydrofuran | 60 | — | — | 30 |
| Example 13 | 0 | hydroxypropyl cellulose | diglyme | 160 | — | — | 80 |
| Comparative Example 1 | 31.1 | hydroxypropyl cellulose | — | — | N-methyl-2-pyrrolidone | — | 30 |
| Comparative Example 2 | | | | | | | |
| Comparative Example 3 | | | | | | | |
| Comparative Example 4 | | | | | | | |
| Comparative Example 5 | | | | | | | |
| Comparative Example 6 | | | | | | | |
| Comparative Example 7 | | | | | | | |

TABLE 2

| | Polylactic Acid-based Resin Microparticles | | | | | | |
|---|---|---|---|---|---|---|---|
| | | Particle Diameter | | | Linseed Oil | Enthalpy of | |
| | Shape of Particle | Number Average Particle Diameter | Particle Diameter Distribution Index | Sphericity | Absorption (ml/100 g) | Fusion (J/g) | Observation Diagram |
| Example 1 | porous | 33 | 1.55 | | 432 | 57.8 | FIG. 1 |
| Example 2 | | 25.1 | 1.35 | 89 | 432 | 57.8 | FIG. 1 |
| Example 3 | | 59.5 | 11.5 | | 661 | | |
| Example 4 | | 13.7 | 1.24 | 82 | 524 | 58.2 | FIG. 2 |
| Example 5 | | 10 | 1.1 | 85 | 96 | 34.3 | FIG. 3 |
| Example 6 | | 14 | 1.25 | 93 | 149 | 32.6 | |
| Example 7 | smooth surface | 1.6 | 1.4 | 95 | 51 | 40.8 | FIG. 4 |
| Example 8 | | 1.8 | 1.82 | 97 | 58 | 30.4 | |
| Example 9 | | 4.5 | 1.1 | 95 | 58 | 0 | FIG. 5 |
| Example 10 | | 7.8 | 1.31 | 91 | | | |
| Example 11 | | 10.2 | 1.20 | 94 | | | |
| Example 12 | | 12.1 | 1.33 | 90 | | | |
| Example 13 | | 10.2 | 1.32 | 94 | 67 | 0 | |
| Comparative Example 1 | x | x | x | x | x | x | x |
| Comparative Example 2 | porous | 64 | 3≤ | 50≥ | | | |
| Comparative Example 3 | | 234.3 | 1.1 | 86 | 86 | 21.2 | FIG. 6 |
| Comparative Example 4 | smooth surface | 6.1 | 17.1 | 94 | 56 | 38.8 | FIG. 7 |
| Comparative Example 5 | | 4.7 | 6.2 | 79 | 54 | 0 | FIG. 8 |
| Comparative Example 6 | x | x | x | x | x | x | x |
| Comparative Example 7 | x | x | x | x | x | x | x |

Example 14

Cosmetic Foundation

A composite was prepared in accordance with a prescription containing 5 mass % of the polylactic acid-based resin microparticles obtained in Example 2, 35 mass % of talc, 30 mass % of mica, 10 mass % of synthetic fluorphlogopite, 5 mass % of titanium oxide, 3 mass % of aluminium hydroxide, 4 mass % of stearic acid, 3 mass % of iron oxide, 0.2 mass % of butyl paraben, 0.1 mass % of methyl paraben, 9 mass % of dimethicone, 1.7 mass % of methicone, and 4 or more mass % of trimethylsiloxysilicate. This composite had a good slidability and a soft feeling of touch.

Example 15

A composite was prepared as in Example 14 except that the polylactic acid-based microparticles obtained in Example 3 were used. This composite had a good slidability and a soft feeling of touch.

Example 16

A composite was prepared as in Example 14 except that the polylactic acid-based microparticles obtained in Example 4 were used. This composite had a good slidability and a soft feeling of touch.

Example 17

A composite was prepared as in Example 14 except that the polylactic acid-based microparticles obtained in Example 5 were used. This composite had a good slidability and a soft feeling of touch.

Comparative Example 8

A composite was prepared as in Example 14 except that no polylactic acid-based microparticles were used. This composite had a low slidability and a coarse feeling of touch.

Example 18

Powder Eye Shadow

A composite was prepared in accordance with a prescription containing 7 mass % of the polylactic acid-based resin in Example 9, 63.6 mass % of synthetic mica, 15 mass % of titanium dioxide coating mica, 6 mass % of glycerin, 4 mass % of squalane, 1.8 mass % of methicone, 0.2 mass % of silica, 2.0 mass % of ultramarine, 0.2 mass % of organic pigment, and 0.2 mass % or more of ethyl paraben. This composite had a good slidability and was glossy in appearance.

Example 19

Cosmetic Foundation

A composite was prepared in accordance with a prescription containing 5 mass % of the polylactic acid-based resin microparticles obtained in Example 9, 35 mass % of talc, 30 mass % of mica, 10 mass % of synthetic fluorphlogopite, 5 mass % of titanium oxide, 3 mass % of aluminium hydroxide, 4 mass % of stearic acid, 3 mass % of iron oxide, 0.2 mass % of butyl paraben, 0.1 mass % of methyl paraben, 9 mass % of dimethicone, 1.7 mass % of methicone, and 4 mass % or more of trimethylsiloxysilicate. Because of its slidability, the composite could spread well, had a non-viscous feeling of touch and was glossy in appearance.

Comparative Examples 9-10

Linseed oil absorptions of commercially available microparticles were evaluated. The results thereof and the results of Examples 2, 3, 4, 5 are shown in Table 3.
Microparticles which have been Used
Comparative Example 9: Nylon microparticles SP-500 (supplied by Toray Industries, Inc.)
Comparative Example 10: Nylon microparticles TR-1 (supplied by Toray Industries, Inc.)

TABLE 3

| | Example 2 | Example 3 | Example 4 | Example 5 | Comparative Example 9 (SP-500) | Comparative Example 10 (TR-1) |
|---|---|---|---|---|---|---|
| Material | Polylactic Acid Microparticles | Polylactic Acid Microparticles | Polylactic Acid Microparticles | Polylactic Acid Microparticles | Nylon 12 | Nylon 6 |
| Linseed Oil Absorption (ml/100 g) | 432 | 661 | 524 | 96 | 72.8 | 135 |

Examples 20-23 and Comparative Examples 11-12

Evaluation as Toner Base Material

Whether the polylactic acid-based resin microparticles prepared in Examples 9-12 can be used as toner base material having low temperature fixation characteristics or not was evaluated from the viewpoint of powder flowability and heat-fusion characteristics at 80 degrees Celsius. The polylactic acid-based resin microparticles prepared in Example 2 and Comparative Example 2 were also evaluated. The evaluation results are shown in Table 4.

The polylactic acid-based resin microparticles of Example 9-12 had a good flowability and were formed into a film shape. In Example 2, the polylactic acid-based resin microparticles did not have sufficient flowability and remained to be in powder shape. In Comparative Example 2, the microparticles had no flowability because of broad particle distribution and low sphericity, and as for heat-fusion characteristics, the microparticles melted and formed into a membrane shape partially but not formed into a film shape.
Powder Flowability An angle (angle of repose) formed between a plane and a ridge line of powders dropped from a powder funnel (made of polypropylene) was measured, and an angle of 50 degrees or less was evaluated as "acceptable." Further, the presence or absence of residues in the funnel was inspected, and powders that no residue remained were evaluated as "excellent." Heat-fusion characteristics at 80 degrees Celsius Putting 100 mg of powders on a hot plate at 80 degrees Celsius for 5 minutes, powders which did not maintain particle shape and formed into a film shape were evaluated as "acceptable," and others were evaluated as "not acceptable."

TABLE 4

| | Polylactic add microparticles | Powder Flowability | | | Fusion Characteristics at 80° C. | |
|---|---|---|---|---|---|---|
| | | Angle of Repose | Residues in funnel | Evaluation | Capability of forming film | Evaluation |
| Example 20 | Example 9 | 30° | remained a bit | acceptable | melted and formed into film shape | acceptable |
| Example 21 | Example 10 | 31° | remained a bit | acceptable | melted and formed into film shape | acceptable |
| Example 22 | Example 11 | 27° | no residue | excellent | melted and formed into film shape | acceptable |
| Example 23 | Example 12 | 25° | no residue | excellent | melted and formed into film shape | acceptable |
| Comparative Example 11 | Example 2 | 70° | remained | not acceptable | remained in powder form | not acceptable |
| Comparative Example 12 | Comparative Example 12 | no flowability | remained | not acceptable | partially melted and formed into membrane shape, but not formed into film shape | not acceptable |

INDUSTRIAL APPLICABILITY

Our porous polylactic acid-based resin microparticles having small particle diameters and high linseed oil absorption capability and the smooth surface polylactic acid-based resin microparticles having spherical shapes and narrow particle diameter distribution are quite useful and practical for various uses in industry. More specifically, these microparticles can be used for, for example, face wash, sunscreen, cleansing agent, cosmetic water, lotion, cosmetic liquid, cream, cold cream, aftershave lotion, shaving soap, oil absorbing sheet, various skin care agents such as matifiant, foundation, foundation powder, liquid foundation, mascara, face powder, Dohran, eyebrow pencil, mascara, eye line, eye shadow, eye shadow base, nose shadow, lipsticks, gloss, cheek brushes, tooth wax, manicure, various cosmetics and various modification agents thereof such as topcoat, shampoo, dry shampoo, conditioner, rinse, shampoo containing rinse ingredients, treatment, hair tonic, hair conditioner, hair oil, pomade, additives for various hair care products such as hair color agent, perfume, cologne, deodorant, baby powder, tooth powder, mouthwash, lip balm, additives for various amenity products such as soap, additive for toner, various rheology-improving agents used for paint and the like, diagnostic test agents for medical purpose, agents for improving machine characteristics of molded products such as car materials and building materials, film, materials for improving machine characteristics of fiber and the like, raw materials for resin molded products used in rapid prototyping, rapid manufacturing and the like, flash-moldable material, paste resin for plastic sol, powder blocking agent, powder flowability improving agent, lubricant, rubber compounding ingredient, polishing agent, viscosity improver, filter material/filter aid, gelatinizer, coagulation agent, additive for paints, oil absorbing material, mold releasing agent, slippage improving agent for plastic films/sheets, antiblocking agent, gloss adjusting agent, frosted finish agent, light diffusion agent, surface hardness improving agent and ductility improving material, spacer for liquid crystal display equipment, filler/carrier for chromatography, base material/additive for cosmetic foundation, assistant for micro-capsules, medical materials for drug delivery system/diagnostic reagents, support agent for perfume/pesticide, catalyst/carrier for chemical reactions, gas adsorption agent, sintered material for ceramic processing, standard particle material for measurement/analysis, particle material for food manufacture industry, material for powder coating, and toner for electrophotographic development.

The invention claimed is:

1. Polylactic acid-based resin microparticles having a number average particle diameter of 1 to 25.1 μm and a linseed oil absorption of 90 ml/100 g or greater, wherein a molar ratio of monomer units of L-lactic acid and D-lactic acid is 90 mole % or more, and said microparticles have a particle diameter distribution index of 1 to 2.

2. The polylactic acid-based resin microparticles according to claim 1, wherein said microparticles comprise a polylactic acid-based resin having an enthalpy of fusion of 5 J/g or greater.

3. Cosmetics which comprise said polylactic acid-based resin microparticles according to claim 1.

4. Polylactic acid-based resin microparticles having a number average particle diameter of 1 to 30 μm, a linseed oil absorption of 100 ml/100 g or greater and a sphericity of 85 or greater, wherein a molar ratio of monomer units of L-lactic acid and D-lactic acid is 90 mole % or more, and said microparticles have a particle diameter distribution index of 1 to 2.

5. The polylactic acid-based resin microparticles according to claim 4, wherein said microparticles comprise a polylactic acid-based resin having an enthalpy of fusion of 5 J/g or greater.

6. Cosmetics which comprise said polylactic acid-based resin microparticles according to claim 4.

* * * * *